US012636259B2

(12) United States Patent
Ichibayashi et al.

(10) Patent No.: US 12,636,259 B2
(45) Date of Patent: May 26, 2026

(54) TRANSDERMAL ABSORPTION PREPARATION

(71) Applicant: Sumitomo Pharma Co., Ltd., Osaka (JP)

(72) Inventors: Eri Ichibayashi, Suita (JP); Masayasu Tanaka, Suita (JP); Yuki Ikeda, Suita (JP); Tomohito Takita, Ibaraki (JP); Kei Tamura, Ibaraki (JP); Tetsuya Nakamura, Ibaraki (JP); Kaiji Fujiwara, Ibaraki (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 643 days.

(21) Appl. No.: 17/904,577

(22) PCT Filed: Feb. 18, 2021

(86) PCT No.: PCT/JP2021/006052

§ 371 (c)(1),
(2) Date: Aug. 18, 2022

(87) PCT Pub. No.: WO2021/166987

PCT Pub. Date: Aug. 26, 2021

(65) Prior Publication Data

US 2023/0091378 A1 Mar. 23, 2023

(30) Foreign Application Priority Data

Feb. 19, 2020 (JP) ................................ 2020-026337
Aug. 5, 2020 (JP) ................................ 2020-132798

(51) Int. Cl.

| | |
|---|---|
| ***A61K 9/70*** | (2006.01) |
| ***A61K 31/19*** | (2006.01) |
| ***A61K 31/496*** | (2006.01) |
| ***A61K 31/506*** | (2006.01) |
| ***A61K 47/02*** | (2006.01) |
| ***A61K 47/10*** | (2017.01) |
| ***A61K 47/12*** | (2006.01) |
| ***A61K 47/14*** | (2017.01) |
| ***A61K 47/18*** | (2017.01) |
| ***A61K 47/22*** | (2006.01) |

(52) U.S. Cl.

CPC ............ *A61K 9/7038* (2013.01); *A61K 31/19* (2013.01); *A61K 31/496* (2013.01); *A61K 31/506* (2013.01); *A61K 47/02* (2013.01); *A61K 47/10* (2013.01); *A61K 47/12* (2013.01); *A61K 47/14* (2013.01); *A61K 47/18* (2013.01); *A61K 47/22* (2013.01)

(58) Field of Classification Search

CPC .... A61K 9/7038; A61K 31/19; A61K 31/506; A61K 47/02; A61K 47/10; A61K 47/12; A61K 47/14; A61K 47/18; A61K 47/22; A16K 31/496

See application file for complete search history.

(56) References Cited

U.S. PATENT DOCUMENTS

| | | | | |
|---|---|---|---|---|
| 5,633,009 | A | 5/1997 | Kenealy et al. | |
| 5,817,331 | A | 10/1998 | Kenealy et al. | |
| 5,837,280 | A | 11/1998 | Kenealy et al. | |
| 6,132,761 | A | 10/2000 | Muraoka et al. | |
| 6,335,031 | B1 * | 1/2002 | Asmussen ............ | A61K 9/7061 604/290 |
| 10,588,973 | B2 | 3/2020 | Miwa et al. | |
| 10,758,535 | B1 | 9/2020 | Kurita et al. | |
| 11,382,978 | B2 | 7/2022 | Miwa et al. | |
| 2006/0110434 | A1 * | 5/2006 | Yamaguchi .......... | A61K 9/7053 514/288 |
| 2006/0193900 | A1 | 8/2006 | Yasukochi et al. | |
| 2007/0232629 | A1 | 10/2007 | Yamaguchi et al. | |
| 2011/0152377 | A1 | 6/2011 | Hanma et al. | |
| 2013/0315977 | A1 * | 11/2013 | Maeda ................ | A61K 31/496 424/443 |
| 2017/0056502 | A1 | 3/2017 | Miwa et al. | |
| 2017/0056503 | A1 | 3/2017 | Hamamoto et al. | |
| 2017/0136025 | A1 | 5/2017 | Jeon et al. | |
| 2018/0185298 | A1 | 7/2018 | Jain et al. | |
| 2018/0236082 | A1 | 8/2018 | Miwa et al. | |

(Continued)

FOREIGN PATENT DOCUMENTS

| | | | | |
|---|---|---|---|---|
| CN | 105997951 | A * | 10/2016 | ............. A61K 31/27 |
| EP | 1743645 | A1 * | 1/2007 | ........... A61K 31/506 |
| JP | 11-79979 | A | 3/1999 | |
| JP | 11-228414 | A | 8/1999 | |
| JP | 2006-169238 | A | 6/2006 | |
| JP | 2006-241179 | A | 9/2006 | |
| JP | 2017-522285 | A | 8/2017 | |
| WO | WO 2005/117886 | A1 | 12/2005 | |
| WO | WO 2008/044336 | A1 | 4/2008 | |
| WO | WO 2010/016219 | A1 | 2/2010 | |
| WO | WO 2017/037812 | A1 | 3/2017 | |

OTHER PUBLICATIONS

Yang Machine Translation (Year: 2016).*

(Continued)

*Primary Examiner* — Scarlett Y Goon

(74) *Attorney, Agent, or Firm* — Oblon, McClelland, Maier & Neustadt, L.L.P.

(57) ABSTRACT

The present invention relates to a transdermal absorption preparation that can maintain a blood concentration sufficient to exert the efficacy of tandospirone, and also shows good storage stability against heat, humidity, and light. According to the present invention, a transdermal absorption preparation containing tandospirone or a pharmaceutically acceptable salt thereof, and levulinic acid, which is superior in the skin permeability of tandospirone or a pharmaceutically acceptable salt thereof in the preparation, and shows good preservation stability against heat and light can be provided.

19 Claims, No Drawings

(56) References Cited

U.S. PATENT DOCUMENTS

| | | | | |
|---|---|---|---|---|
| 2019/0284205 | A1* | 9/2019 | Trower | A61P 15/00 |
| 2020/0171156 | A1 | 6/2020 | Miwa et al. | |
| 2021/0060015 | A1 | 3/2021 | Kurita et al. | |
| 2021/0386739 | A1 | 12/2021 | Kurita et al. | |
| 2022/0062282 | A1 | 3/2022 | Kurita et al. | |
| 2022/0193075 | A1 | 6/2022 | Kurita et al. | |

OTHER PUBLICATIONS

Yasushi Kawasaki, et al.; Toxicity Study of a Rubber Antioxidant, 2-mercaptobenzimadizole, by repeated oral administration to rats; The Journal of Toxicological Sciences; vol. 23, No. 1,53-68; 1998 (Year: 1998).*

Aarti Naik, et al.; Mechanism of oleic acid-induced skin penetration enhancement in vivo in humans; Journal of Controlled Release; 37 (1995) 299-306; Published 1995 (Year: 1995).*

S. Mojtaba Taghizadeh, et al.; A statistical experimental design approach to evaluate the influence of various penetration enhancers on transdermal drug delivery of buprenorphine; Journal of Advanced Research; vol. 6, Iss. 2, pp. 155-162; Published Mar. 2015 (Year: 2015).*

CAS Registry No. 87760-53-0 Tandospirone (1984). Property data retrieved from STN on Sep. 5, 2025.*

Yang (2016) English translation of CN105997951. Retrieved from <https://worldwide.espacenet.com/> Retrieved on Sep. 2, 2025.*

International Search Report issued Apr. 6, 2021, in PCT/JP2021/006052 filed Feb. 18, 2021, 3 pages.

Tandospirone, Drugbank, https://go.drugbank.com/drugs/DB12833, particularly, item of Properties, Drug created at Oct. 21, 2016 and Updated at Feb. 21, 2021, 4 pages.

Utsumi S., et al., “Effect of Nerolidol and/or Levulinic Acid on the Thermotropic Behavior of Lipid Lamellar Structures in the Stratum Corneum”, Chem. Pharm. Bull, vol. 64, No. 12, 2016, pp. 1692-1697.

* cited by examiner

TRANSDERMAL ABSORPTION PREPARATION

CROSS-REFERENCE TO RELATED APPLICATIONS

The present application is a 35 U.S.C. § 371 national stage patent application of International patent application PCT/JP2021/006052, filed on Feb. 18, 2021, which is based on and claims the benefits of priority to Japanese Application No. 2020-026337, filed on Feb. 19, 2020 and Japanese Application No. 2020-132798, filed on Aug. 5, 2020. The entire contents of all of the above applications are incorporated herein by reference.

TECHNICAL FIELD

The present invention relates to a transdermal absorption preparation containing tandospirone or a pharmaceutically acceptable salt thereof.

BACKGROUND ART (1R,2S,3R,4S)—N-[4-[4-(pyrimidin-2-yl)piperazin-1-yl]butyl]-2,3-bicyclo[2.2.1]heptan dicarboxyimide (generic name "tandospirone") is a selective serotonin 1A receptor agonist. In Japan, tandospirone citrate tablet (trade name: Sediel (registered trade mark) tablet) is commercially available as an antianxiety drug.

Patent documents 1 to 3 disclose transdermal absorption preparations containing tandospirone.

DOCUMENT LIST

Patent Documents

[Patent Document]
JP-A-11-228414
[Patent Document]
WO2005/117886
[Patent Document]
WO2008/044336

SUMMARY OF INVENTION

Problems to be Solved by the Invention

The present invention provides a tandospirone-containing transdermal absorption preparation that shows improved skin permeability of tandospirone and superior preservation stability of the preparation.

Means of Solving the Problems

The present inventors have conducted intensive studies and found that the skin permeability of tandospirone is improved by blending levulinic acid, based on which they have made it possible to reduce the amount of a tandospirone-containing transdermal absorption preparation to be applied or sprayed, or reduce the area of the preparation. In addition, they have found that the use of levulinic acid in combination with a specific additive (iii) affords a synergistic effect in the improvement of the skin permeability of tandospirone.

The present inventors have further conducted intensive studies and found that a transdermal absorption preparation with good stability can be obtained while maintaining the improvement of the skin permeability of tandospirone, by blending a specific additive (iv). The present invention is superior on this point as well.

Accordingly, the present invention provides the following.

[1] A transdermal absorption preparation having a transdermal absorption layer, wherein the transdermal absorption layer comprises (i) tandospirone or a pharmaceutically acceptable salt thereof, and (ii) levulinic acid or a pharmaceutically acceptable salt thereof (hereinafter sometimes to be referred to as "the transdermal absorption preparation of the present invention").

[2] The transdermal absorption preparation of the above-mentioned [1], wherein the preparation is in the form of a patch preparation (hereinafter sometimes to be referred to as "the patch preparation of the present invention").

[3] The transdermal absorption preparation of the above-mentioned [1] or [2], further comprising (iii) one kind or two or more kinds of additives selected from the group consisting of polyhydric alcohol fatty acid ester and fatty acid amide.

[4] The transdermal absorption preparation of any of the above-mentioned [1] to [3], wherein the aforementioned transdermal absorption layer comprises oleic acid.

[5] The transdermal absorption preparation of any of the above-mentioned [1] to [4], further comprising (iv) one kind or two or more kinds of additives selected from the group consisting of 2,6-di-tert-butyl-4-methylphenol, sodium thiosulfate, 2-mercaptobenzimidazole, propyl gallate, α-tocopherol, sodium sulfite, and sodium bisulfite.

[6] The transdermal absorption preparation of any of the above-mentioned [1] to [5], wherein the (i) is tandospirone.

[7] The transdermal absorption preparation of any of the above-mentioned [1] to [6], wherein the (ii) is levulinic acid.

[8] The transdermal absorption preparation of any of the above-mentioned [5] to [7], wherein the (iv) comprises 2,6-di-tert-butyl-4-methylphenol.

[9] The transdermal absorption preparation of any of the above-mentioned [5] to [8], wherein the (iv) comprises 2,6-di-tert-butyl-4-methylphenol and sodium thiosulfate.

[10] The transdermal absorption preparation of any of the above-mentioned [3] to [9], wherein the (iii) comprises polyhydric alcohol fatty acid ester.

[11] The transdermal absorption preparation of any of the above-mentioned [3] to [10], wherein the (iii) comprises propylene glycol fatty acid ester.

[12] The transdermal absorption preparation of any of the above-mentioned [1] to [11], further comprising (v) monohydric alcohol fatty acid ester.

[13] The transdermal absorption preparation of the above-mentioned [12], wherein the aforementioned (v) monohydric alcohol fatty acid ester is isopropyl myristate and/or isopropyl palmitate.

[14] The transdermal absorption preparation of any of the above-mentioned [1] to [13], wherein a content of the (i) in 100 wt % of the aforementioned transdermal absorption layer is 0.1 to 30 wt %.

[15] The transdermal absorption preparation of any of the above-mentioned [1] to [14], wherein a content of the (ii) in 100 wt % of the aforementioned transdermal absorption layer is 0.1 to 20 wt %.

[16] The transdermal absorption preparation of any of the above-mentioned [1] to [14], wherein the content of the (ii) in 100 wt % of the aforementioned transdermal absorption layer is 3 to 10 wt %.

[17] The transdermal absorption preparation of any of the above-mentioned [1] to [14], wherein the content of the (ii) in 100 wt % of the aforementioned transdermal absorption layer is 6 to 7 wt %.

[18] The transdermal absorption preparation of any of the above-mentioned [5] to [17], wherein a content of the (iv) 2,6-di-tert-butyl-4-methylphenol in 100 wt % of the aforementioned transdermal absorption layer is 0.001 to 10 wt %.

[19] The transdermal absorption preparation of any of the above-mentioned [5] to [18], wherein a content of the (iv) sodium thiosulfate in 100 wt % of the aforementioned transdermal absorption layer is 0.001 to 7 wt % based on anhydrate.

[20] The transdermal absorption preparation of any of the above-mentioned [5] to [19], wherein a content of the (iv) 2-mercaptobenzimidazole in 100 wt % of the aforementioned transdermal absorption layer is 0.001 to 5 wt %.

[21] The transdermal absorption preparation of any of the above-mentioned [5] to [20], wherein a content of the (iv) propyl gallate in 100 wt % of the aforementioned transdermal absorption layer is 0.001 to 7 wt %.

[22] The transdermal absorption preparation of any of the above-mentioned [3] to [21], wherein a content of the (iii) polyhydric alcohol fatty acid ester in 100 wt % of the aforementioned transdermal absorption layer is 1 to 20 wt %.

[23] The transdermal absorption preparation of any of the above-mentioned [2] to [22], wherein the preparation is a patch preparation and the transdermal absorption layer is an adhesive layer.

[24] The transdermal absorption preparation of the above-mentioned [23], wherein the aforementioned adhesive layer comprises an acrylic polymer, and a weight ratio of the acrylic polymer and the total of organic liquid components in the adhesive layer is 1:2.33 to 1:0.25.

[25] A transdermal absorption preparation comprising (i) tandospirone or a pharmaceutically acceptable salt thereof, and one kind or two or more kinds of additives selected from the group consisting of an aprotic polar solvent, an organic acid (excluding levulinic acid and acetic acid), a non-ionic surfactant, and higher alcohol ester.

[26] The transdermal absorption preparation of the above-mentioned [25], wherein the organic acid is oleic acid.

[27] A transdermal absorption preparation comprising (i) tandospirone or a pharmaceutically acceptable salt thereof, and (iv) one kind or two or more kinds of additives selected from the group consisting of 2,6-di-tert-butyl-4-methylphenol, sodium thiosulfate, 2-mercaptobenzimidazole, propyl gallate, α-tocopherol, sodium sulfite, and sodium bisulfite.

[28] A composition for stabilizing a medicament comprising (i) tandospirone or a pharmaceutically acceptable salt thereof, and (ii) levulinic acid or a pharmaceutically acceptable salt thereof, wherein the composition comprises at least one component selected from the group consisting of 2,6-di-tert-butyl-4-methylphenol, sodium thiosulfate, 2-mercaptobenzimidazole, propyl gallate, α-tocopherol, sodium sulfite, and sodium bisulfite.

[29] A composition for improving skin permeability of (i) tandospirone or a pharmaceutically acceptable salt thereof, wherein the composition comprises (ii) levulinic acid or a pharmaceutically acceptable salt thereof, and (iii) polyhydric alcohol fatty acid ester or fatty acid amide.

Effect of the Invention

According to the present invention, a tandospirone-containing transdermal absorption preparation that shows superior skin permeability of tandospirone or a pharmaceutically acceptable salt thereof in a preparation, and can maintain a blood concentration sufficient to exhibit efficacy of tandospirone when in use can be provided. Furthermore, a tandospirone-containing transdermal absorption preparation that shows good preservation stability of tandospirone or a pharmaceutically acceptable salt thereof in the preparation against heat, humidity, and light, and affords easy manufacturability and easy quality management can be provided.

DESCRIPTION OF EMBODIMENTS

Preferable embodiments of the present invention are explained in detail in the following.

In the present invention, the dosage form of the transdermal absorption preparation is not particularly limited as long as it is a dosage form conventionally used for external preparations. For example, the dosage forms described in the Japanese Pharmacopoeia, 17th Edition, can be mentioned. It is preferably ointment, cream, gel, gel-like cream, spray (e.g., external aerosol agent, pump spray agent), external liquid (liniment or lotion), or patch preparation, more preferably ointment or patch preparation, further preferably patch preparation.

The patch preparation means a preparation in general which can be adhered to the skin. In the present invention, the shape of the patch preparation is not limited, and may be, for example, tape, sheet, or the like. Specific examples of the patch preparation include tape preparation, patch preparation, cataplasm preparation, plaster preparation, and the like.

Generally, a patch preparation has a sheet-like structure composed of three layers of a backing film, an adhesive layer, and a release film (liner). As the backing film, nonwoven fabric, knit, plastic film, and the like are used. The adhesive layer is a main component containing an active ingredient and an adhesive, and has an appropriate adhesive force. The release film is a coating material that protects an adhesive surface of the adhesive layer until use, and polypropylene, polyethylene, cellophane, polyester, release paper, and the like are used. Generally, the adhesive layer is stored as a structure in which it is sandwiched between the backing film and the release film, and used by adhering an adhesive surface of the adhesive layer to the skin after peeling off the release film.

In the present invention, the transdermal absorption layer means the composition of a part directly contacted with the skin. When the transdermal absorption preparation is ointment, cream, gel, gel-like cream, lotion, spray, aerosol or liniment, the transdermal absorption layer is the preparation composition itself. The transdermal absorption layer contains (i) tandospirone or a pharmaceutically acceptable salt thereof. It can further contain additives (ii), (iii), (iv), (v), and/or other additives.

When the transdermal absorption preparation is a patch preparation, the transdermal absorption layer means an adhesive layer. The adhesive layer contains (i) tandospirone or a pharmaceutically acceptable salt thereof, and an adhesive base. It can further contain additives (ii), (iii), (iv), (v), and/or other additives.

(Active Ingredient Drug)

(i) (1R,2S,3R,4S)—N-[4-[4-(pyrimidin-2-yl)piperazin-1-yl]butyl]-2,3-bicyclo[2.2.1]heptan dicarboxyimide (generic name "tandospirone"), which is an active ingredient drug contained in the transdermal absorption preparation of the present invention, is a compound represented by the following formula:

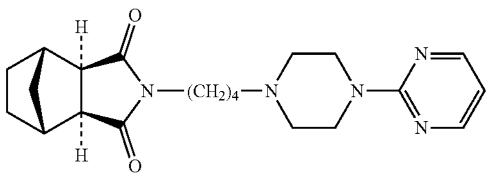

(hereinafter sometimes to be referred to as "compound A"), and is a selective serotonin 1A receptor agonist. Tandospirone citrate is commercially available as an antianxiety drug (sediel (registered trade mark) tablet).

The active ingredient drug in the present invention may be compound A (tandospirone free base) or a pharmaceutically acceptable salt thereof. Examples of the pharmaceutically acceptable salt include salts with organic acids such as formate, acetate, propionate, succinate, lactate, malate, adipate, citrate, tartrate, methanesulfonate, fumarate, maleate, p-toluenesulfonate, ascorbate, and the like; salts with inorganic acids such as hydrochloride, hydrobromide, sulfate, nitrate, phosphate, and the like, and the like. In addition, compound A or a pharmaceutically acceptable salt thereof may be either a solvate (e.g., hydrate, ethanol solvate, propylene glycol solvate) or a non-solvate.

The above-mentioned compound A or a pharmaceutically acceptable salt thereof can be produced according to, for example, the method described in JP-A-58-126865 or a method analogous thereto. The produced compound A or a pharmaceutically acceptable salt thereof may be pulverized as appropriate according to a conventional method.

While the content of the "compound A or a pharmaceutically acceptable salt thereof" to be contained in the transdermal absorption preparation of the present invention needs to be determined according to the age, symptom and the like of the patient who receives the administration, and is not particularly limited, it is generally about 0.1 to about 30 wt %, preferably about 0.1 to about 20 wt %, more preferably about 0.1 to about 15 wt %, in terms of compound A (free base of tandospirone) in 100 wt % of the transdermal absorption layer.

When the transdermal absorption preparation is a patch preparation, it is generally about 0.1 to about 30 wt %, preferably about 0.1 to about 20 wt %, more preferably about 0.1 to about 15 wt %, further preferably 1 to 10 wt %, further more preferably 2 to 8 wt % of an adhesive layer as 100 wt %, though subject to change depending on the area of the patch preparation.

Here, "in terms of compound A" means that, when compound A is in the form of a salt or compound A contains crystal water, the amount corresponding to the salt or the crystal water is not included in the weight of compound A. In other words, it means that the amount of a salt of compound A or a hydrate thereof is calculated by converting the weight thereof to the weight of an equimolar amount of compound A (free base non-hydrate).

(Levulinic Acid)

The levulinic acid used in the present invention is an organic acid classified as keto acid. The levulinic acid used in the present invention is a free acid of levulinic acid (that is, levulinic acid itself), and additive (ii) used in the present invention may be provided as a free acid of levulinic acid (that is, levulinic acid itself) or a pharmaceutically acceptable salt thereof. Examples of the pharmaceutically acceptable salt include alkali metal salts such as sodium salt, potassium salt, and the like, and the like. As the levulinic acid or a pharmaceutically acceptable salt thereof, a commercially available product may be used as it is, or a pharmaceutically acceptable salt thereof prepared from levulinic acid according to a method known per se may be used. As the (ii) levulinic acid or a pharmaceutically acceptable salt thereof used in the present invention, levulinic acid is preferred.

In the transdermal absorption preparation of the present invention, when the content of levulinic acid or a pharmaceutically acceptable salt thereof in the transdermal absorption layer is too low, the drug (i.e., compound A or a pharmaceutically acceptable salt thereof) tends to show an insufficient skin permeability-promoting effect, or a part of compound A or a pharmaceutically acceptable salt thereof tends to become a crystal state during production or during storage. When the content of levulinic acid or a pharmaceutically acceptable salt thereof in the transdermal absorption layer is too high, skin irritation tends to increase. Therefore, the content of the levulinic acid or a pharmaceutically acceptable salt thereof in the transdermal absorption layer is preferably 0.1 to 20 wt %, more preferably 0.5 to 15 wt %, further preferably 1 to 10 wt %, most preferably 3 to 8 wt %, in terms of levulinic acid (free acid of levulinic acid) in 100 wt % of the transdermal absorption layer. From the aspect of promotion of skin permeability of a drug, it is preferably not less than 0.5 wt %, more preferably not less than 1 wt %, further preferably not less than 3 wt %. From the aspect of skin irritation, it is preferably not more than 15 wt %, more preferably not more than 10 wt %. Specifically, the lower limit of the content of levulinic acid or a pharmaceutically acceptable salt thereof in the transdermal absorption layer is 0.1 wt %, 0.5 wt %, 1 wt %, 3 wt %, 4 wt %, 5 wt %, or 6 wt %, and the upper limit thereof is 20 wt %, 15 wt %, 10 wt %, 8 wt %, or 7 wt %, in terms of levulinic acid (free acid of levulinic acid) in 100 wt % of the transdermal absorption layer.

Here, "in terms of levulinic acid" means that, when levulinic acid is in the form of a salt, the amount corresponding to the salt is not included in the weight of levulinic acid. In other words, it means that the amount of a salt of levulinic acid is calculated by converting the weight thereof to the weight of an equimolar amount of levulinic acid (free acid).

When the transdermal absorption preparation is a patch preparation, the content of levulinic acid or a pharmaceutically acceptable salt thereof in 100 wt % of the "transdermal absorption layer" can be rephrased as the content of levulinic acid or a pharmaceutically acceptable salt thereof in the "adhesive layer".

(Polyhydric Alcohol Fatty Acid Ester and Fatty Acid Amide)

The additive (iii) used in the present invention can be selected from the group consisting of polyhydric alcohol fatty acid ester and fatty acid amide. Preferably, one kind or two or more kinds selected from polyhydric alcohol fatty acid esters can be used.

Examples of the polyhydric alcohol fatty acid ester include polyoxyethylene sorbitan fatty acid ester, sorbitan fatty acid ester, polyoxyethylene fatty acid ester, glycerol fatty acid ester, propylene glycol fatty acid ester, and the like. Among these, glycerol fatty acid ester, propylene glycol fatty acid ester, and diethylene glycol fatty acid ester are preferred, glycerol fatty acid ester and propylene glycol fatty acid ester are more preferred, and propylene glycol fatty acid ester is particularly preferred.

Examples of the fatty acid amide include lauric acid diethanolamide, coconut oil fatty acid N-methylethanol amide, and the like.

Examples of the glycerol fatty acid ester include glycerol tricaprylate, glycerol caprylate, glycerol triacetate, glyceril monocaprylate, glyceril caprylate, glyceril oleate, glyceril stearate, glycerol monolinoleate, glycerol monooleate, glycerol stearate, and the like. Examples of the propylene glycol fatty acid ester include propylene glycol dicaprate, propylene glycol dilaurate, propylene glycol monolaurate, propylene glycol monocaprylate, and the like (preferably, propylene glycol monolaurate and propylene glycol monocaprylate). One kind or two or more kinds of the polyhydric alcohol fatty acid esters can be used in combination.

In the transdermal absorption preparation of the present invention, the content of the polyhydric alcohol fatty acid ester or fatty acid amide in the transdermal absorption layer is not particularly limited, and is preferably 1 to 20 wt % in 100 wt % of the transdermal absorption layer. From the aspect of skin irritation, the content of the polyhydric alcohol fatty acid ester or fatty acid amide in the transdermal absorption layer is more preferably 1 to 15 wt % in 100 wt % of the transdermal absorption layer.

Specifically, the lower limit of the content of the polyhydric alcohol fatty acid ester or fatty acid amide in the transdermal absorption layer is 1 wt %, 1.5 wt %, 3 wt %, or 5 wt %, and the upper limit thereof is 20 wt %, 18 wt %, 15 wt %, or 13 wt %, in 100 wt % of the transdermal absorption layer.

When the transdermal absorption preparation is a patch preparation, the content of the polyhydric alcohol fatty acid ester or fatty acid amide in 100 wt % of the "transdermal absorption layer" can be rephrased as the content of the polyhydric alcohol fatty acid ester or fatty acid amide in the "adhesive layer".

The additive components composed of (ii) levulinic acid and (iii) polyhydric alcohol fatty acid ester or fatty acid amide used in the present invention is hereinafter referred to as "additive A group". The combination of the "additive A group" has afforded an effect of promoting the skin permeation of compound A or a pharmaceutically acceptable salt thereof.

(Stabilizer)

The additive (iv) (hereinafter sometimes to be referred to as "additive B group") used in the present invention can be selected from the group consisting of 2,6-di-tert-butyl-4-methylphenol, sodium thiosulfate, 2-mercaptobenzimidazole, propyl gallate, α-tocopherol, sodium sulfite, and sodium bisulfite. The additive B group is preferably selected from 2,6-di-tert-butyl-4-methylphenol, sodium thiosulfate and 2-mercaptobenzimidazole, more preferably selected from 2,6-di-tert-butyl-4-methylphenol and sodium thiosulfate.

The stabilizing effect on compound A or a pharmaceutically acceptable salt thereof in the preparation can be obtained by adding only one kind of additive contained in the additive B group, and can also be obtained by adding two or more kinds of additives selected from the additive B group in combination. Particularly, a combination of two or more kinds selected from 2,6-di-tert-butyl-4-methylphenol, sodium thiosulfate, and 2-mercaptobenzimidazole is preferred because a synergistic stabilizing effect on compound A in the preparation can be obtained. As used herein, the stabilizing effect means an effect of improving the stability (preservation stability) of compound A in the transdermal absorption preparation of the present invention against heat, humidity and/or light. For example, an effect of suppressing a decrease in the content of compound A, an effect of suppressing the formation of analogues, an effect of suppressing discoloration of the preparation, and the like, when it is heated at 40° C., 50° C. and 60° C. for a certain period of time, when humidified for a certain period of time (25° C. 60% RH, 40° C. 75% RH conditions, etc.), and when exposed to light for a certain period of time, during production or storage of the preparation can be mentioned.

When the content of the additive of the additive B group in the transdermal absorption layer is too low, the stabilizing effect of compound A or a pharmaceutically acceptable salt thereof tends to be insufficient. When it is too high, the additive of the additive B group in the transdermal absorption layer separates from the other components, and prevents production of a patch preparation. Therefore, the content of the additive of the additive B group in the transdermal absorption layer is preferably 0.001 to 10 wt % in 100 wt % of the transdermal absorption layer. The content of 2,6-di-tert-butyl-4-methylphenol is generally 0.001 to 10 wt %, preferably 0.005 to 10 wt %, more preferably 0.01 to 10 wt %, further preferably 0.01 to 8 wt %, in 100 wt % of the transdermal absorption layer. The content of sodium thiosulfate is generally 0.001 to 7 wt %, preferably 0.001 to 5 wt %, more preferably 0.001 to 3 wt %, further preferably 0.001 to 2 wt %, in 100 wt % of the transdermal absorption layer. The content of 2-mercaptobenzimidazole is generally 0.001 to 5 wt %, preferably 0.05 to 5 wt %, more preferably 0.1 to 5 wt %. In addition, the content of propyl gallate is preferably 0.001 to 7 wt %, more preferably 0.001 to 5 wt %, in 100 wt % of the transdermal absorption layer. When the additives of the additive B group are used in combination, the total content of two or more kinds of additives selected from additive B group is preferably 0.002 to 15 wt %, more preferably 0.005 to 10 wt %, in 100 wt % of the transdermal absorption layer. The total content when 2,6-di-tert-butyl-4-methylphenol and sodium thiosulfate are contained is preferably 0.002 to 10 wt %, more preferably 0.002 to 8 wt %, in 100 wt % of the transdermal absorption layer. The total content of 2,6-di-tert-butyl-4-methylphenol and 2-mercaptobenzimidazole is preferably 0.05 to 10 wt % in 100 wt % of the transdermal absorption layer.

As the content ratio of the combination of these additives, the content ratio of 2,6-di-tert-butyl methylphenol and sodium thiosulfate is preferably 1:0.001 to 1:1000, more preferably 1:0.005 to 1:500, further preferably 1:0.01 to 1:50, in weight ratio. The content ratio of 2,6-di-tert-butyl-4-methylphenol and 2-mercaptobenzimidazole is preferably 1:0.01 to 1:500, more preferably 1:0.1 to 1:100, further preferably 1:0.5 to 1:50, in weight ratio.

When the transdermal absorption preparation is a patch preparation, the content of the additive B group in 100 wt % of the "transdermal absorption layer" can be rephrased as the content of the additive B group in the "adhesive layer".

(Organic Liquid Component)

In the patch preparation of the present invention, an organic liquid component is preferably contained in the adhesive layer so as to further soften the adhesive layer and reduce physical skin irritation during adhesion and/or detachment.

In the patch preparation of the present invention, to further soften the adhesive layer, and reduce physical skin irritation during adhesion and/or detachment, the content ratio of the adhesive base and the total of organic liquid components in the adhesive layer is preferably 1:2.33 to 1:0.25 in weight ratio (wt % ratio of adhesive base:total of organic liquid components) and, from the aspect of manufacturability, more preferably 1:2.33 to 1:0.66. In addition, the adhesiveness is improved and the skin irritation at the time of peeling off is also improved by increasing the component ratio of the adhesive base in the adhesive layer. Thus, from the aspect of skin adhesive force, content ratio of the adhesive base and the total of organic liquid components is more preferably 1:1.86 to 1:0.66 and, from the aspect of skin irritation, more preferably 1:1.86 to 1:1.

In the patch preparation of the present invention, to further soften the adhesive layer, and reduce physical skin irritation during adhesion and/or detachment, the content ratio of the acrylic polymer and the total of organic liquid components in the adhesive layer is preferably 1:2.33 to 1:0.25 in weight ratio (wt % ratio of acrylic polymer form:total of organic liquid components). From the aspect of skin adhesiveness, the content ratio (wt % ratio) of the acrylic polymer and the total of organic liquid components in the adhesive layer is preferably 1:1.86 to 1:0.66.

In the present invention, the weight of the total of the organic liquid components means, as described later, the total weight of the components corresponding to "liquid", "liquid (partially precipitated)", "liquid state", "oily" or "soft paste" within the range of 25° C.±5° C. The organic liquid components including the below-mentioned specific examples are calculated as the organic liquid component.

The organic liquid component in the present invention is an organic substance which itself is a liquid at room temperature (25° C.), shows an action to plasticize the adhesive layer, and is compatible with an adhesive polymer constituting the above-mentioned adhesive. As used herein, the "liquid state" means that it can be used as a liquid by appropriately warming to the extent that does not impair the quality in formulating a preparation. It is used in the meaning including those that are liquid at 25° C., as well as those showing partial precipitation, those showing partial solidification, and the like. For example, in the manual of the below-mentioned specific additives (commercially available products), those described as "Liquid", "liquid", "liquid (partially precipitated)", "liquid state", "oily" or "soft paste" within the range of 25° C.±5° C. are included in the "liquid state" in the present specification.

In the present invention, specific examples of the organic liquid component include fatty acid esters of fatty acid having a carbon number of 8 to 18 (preferably, 12 to 16) and monohydric alcohol having a carbon number of 1 to 18 (hereinafter to be also abbreviated as "C8-18(12-16)-C1-18 fatty acid ester"), such as isopropyl myristate, ethyl laurate, isopropyl palmitate, ethyl oleate, isostearyl laurate, isotridecyl myristate, octyl palmitate, diisopropyl adipate, cetyl lactate, oleyl oleate, cetyl ethylhexanoate, octyldodecyl myristate, butyl stearate, 2-ethylhexyl stearate, n-butyl acetate, diethyl sebacate, and the like; fatty acid esters of fatty acid having a carbon number of 8 to 18 and polyhydric alcohol having a carbon number of 1 to 18, such as glycerol fatty acid ester, propylene glycol fatty acid ester, polyethylene glycol fatty acid ester, sucrose fatty acid ester, and the like; fatty acid amides such as lauric acid diethanol amide, coconut oil fatty acid N-methylethanol amide, and the like; organic acids such as fatty acid (e.g., caprylic acid (octanoic acid, C8), caproic acid, pelargonic acid (nonanoic acid, C9), acetic acid, propionic acid, isobutyric acid, levulinic acid, lactic acid, oleic acid etc.), alkylsulfonic acid (methanesulfonic acid, ethanesulfonic acid, polyoxyethylene ether sulfonic acid, etc.), and the like; glycols such as ethylene glycol, diethylene glycol, triethylene glycol, polyethylene glycol, 1,3-propanediol, polypropylene glycol, and the like; fats and oils such as olive oil, castor oil, coconut oil, sesame oil, squalene, and the like; organic solvents such as dimethyl sulfoxide, dimethylformamide, dimethylacetamide, dimethyllauryl amide, dodecylpyrrolidone, isosorbitol, oleyl alcohol, lauric acid, N-methyl-2-pyrrolidone, and the like; liquid surfactants such as sodium polyoxyethylene alkyl ether sulfate, sodium polyoxyethylene lauryl ether sulfate, sodium alkylnaphthalene sulfonate, polyoxyethylene oleylamine, sodium polyoxyethylene oleyl ether phosphate, polyoxyl stearate, decaglyceril laurate, polyoxyethylene sorbitan monolaurate, polyoxyethylene sorbitan monostearate, polyoxyethylene lauryl ether (lauromacrogol), sorbitan monolaurate, sorbitan trioleate, polyoxyethylene sorbit tetraoleate, glycerol monooleate, tocopherol, and the like; hydrocarbons such as gelled hydrocarbon, liquid paraffin, and the like; known plasticizer; and ethoxylated stearyl alcohol, glycerol, and the like. One kind or two or more kinds of the organic liquid components can be used in combination. The organic liquid component in the present invention preferably contains C8-18(12-16)-C1-18 fatty acid ester, particularly preferably isopropyl myristate or isopropyl palmitate.

(Crosslinking Agent)

In the patch preparation of the present invention, a crosslinking treatment can be applied to the adhesive layer. The crosslinking treatment is not particularly limited and can be performed by a means generally performed in this field of the art, such as a chemical crosslinking treatment (crosslinking treatment using a crosslinking agent and the like), a physical crosslinking treatment (crosslinking treatment by irradiation of electron beam such as gamma ray, irradiation of ultraviolet light and the like) and the like. By the crosslinking treatment, the adhesive layer becomes a so-called adhesive layer in a gel state, which has suitable adhesiveness and cohesive force, while providing a soft feeling to the skin. In the patch preparation of the present invention, when a chemical crosslinking treatment or a physical crosslinking treatment is applied to the adhesive layer, stability of compound A or a pharmaceutically acceptable salt thereof tends to decrease during the production steps or storage of the preparation (that is, the production amount of analogue tends to increase). It has been confirmed in the present invention that the stability of compound A or a pharmaceutically acceptable salt thereof is improved by blending the above-mentioned additive B group in an acrylic polymer that underwent a crosslinking treatment.

When a chemical crosslinking treatment using a crosslinking agent is applied to the adhesive layer, crosslinking can be effectively caused by adding a crosslinking agent to the adhesive layer, though self-crosslinking can also be induced in the adhesive layer. The crosslinking agent is not particularly limited as long as it does not permit formation of crosslinking to be prevented by compound A or a pharmaceutically acceptable salt thereof. Examples thereof include peroxides (e.g., benzoyl peroxide (BPO) etc.), isocyanate compounds, organometallic compounds (e.g., zirconium, zinc, zinc acetate etc.), metal alcoholates (e.g., tetraethyltitanate, tetraisopropyltitanate, aluminum isopropylate, aluminum sec-butyrate etc.), metal chelate compounds (e.g., aluminum ethylacetoacetate diisopropylate, titanium diisopropoxide bis(acetylacetonate), tetraoctylene glycol titanium, aluminum isopropylate, ethylacetoacetate aluminum diisopropylate, aluminum tris(ethylacetoacetate), aluminum tris (acetylacetonate)), and the like. In particular, the crosslinking agent to be contained in the adhesive layer is preferably a metal chelate compound because a decrease in the cohesive force of the adhesive layer during adhesion of the patch preparation of the present invention to the human skin can be reduced, and cohesive failure does not easily occur during detachment of the adhesive layer. One kind or two or more kinds of the crosslinking agents may be used in combination.

When the adhesive layer is subjected to a chemical crosslinking treatment using a crosslinking agent, the amount of the crosslinking agent varies depending on the kinds of crosslinking agent and adhesive polymer. It is generally preferably 0.01 to 10 wt %, more preferably 0.05 to 5 wt %, in 100 wt % of the adhesive layer. When the amount of the crosslinking agent is less than 0.01 wt % with respect to 100 wt % of the adhesive layer, a sufficient cohesive force cannot be conferred to an adhesive layer since the crosslinking points are too few, which in turn may result in adhesive residue and strong skin irritation caused by cohesive failure during the detachment of the patch preparation from the skin. When the amount of the crosslinking agent is more than 10 wt % with respect to 100 wt % of the adhesive layer, sufficient skin adhesion may not be afforded, though the cohesive force is high. In addition, skin irritation may occur due to the residual unreacted crosslinking agent. For example, the chemical crosslinking treatment can be carried out by, after addition of the crosslinking agent to the adhesive layer, steps of heating to the crosslinking reaction temperature or higher and preserving the layer, that is, an aging step. While the heating temperature therefor is appropriately determined according to the kind of the crosslinking agent, it is preferably 60 to 90° C., more preferably 60 to 80° C. The heating time is preferably 12 to 96 hr, more preferably 24 to 72 hr.

In the present invention, the aprotic polar solvent, is not particularly limited and can be selected from, for example, N-methyl-2-pyrrolidone, dimethylacetamide, dimethyllauryl amide, and the like.

In addition, the non-ionic surfactant is not particularly limited and can be selected from, for example, lauromacrogol, sorbitan monolaurate, polysorbate 80, polysorbate 20, and the like.

The organic acid (excluding levulinic acid and acetic acid) is not particularly limited as long as it is other than levulinic acid and acetic acid, and fatty acid, aromatic carboxylic acid, alkylsulfonic acid, cholic acid derivative, and the like can be mentioned. Specific examples of the fatty acid include propionic acid, citric acid, isobutyric acid, caproic acid, caprylic acid, lactic acid, maleic acid, oleic acid, pyruvic acid, oxalic acid, succinic acid, tartaric acid, and the like. Examples of the aromatic carboxylic acid include phthalic acid, salicylic acid, benzoic acid, acetylsalicylic acid, and the like, examples of the alkylsulfonic acid include methanesulfonic acid, ethanesulfonic acid, propylsulfonic acid, butanesulfonic acid, polyoxyethylene alkyl ether sulfonic acid and the like, and examples of the cholic acid derivative include dehydrocholic acid and the like. The organic acid (excluding levulinic acid and acetic acid) is preferably fatty acid, particularly preferably oleic acid.

The higher alcohol ester is not particularly limited and can be selected from, for example, diisopropyl adipate, oleyl oleate, diethyl sebacate, and the like.

The content of the aprotic polar solvent in the transdermal absorption layer is preferably 0.1 to 20 wt %, more preferably 0.5 to 15 wt %, further preferably 1 to 10 wt %, in 100 wt % of the transdermal absorption layer.

The content of the non-ionic surfactant in the transdermal absorption layer is preferably 0.1 to 20 wt %, more preferably 0.5 to 15 wt %, further preferably 1 to 10 wt %, in 100 wt % of the transdermal absorption layer.

The content of the organic acid (excluding levulinic acid and acetic acid) in the transdermal absorption layer is preferably 0.1 to 30 wt %, more preferably 0.1 to 25 wt %, further preferably 0.1 to 20 wt %, further more preferably 0.1 to 15 wt %, in 100 wt % of the transdermal absorption layer. In another embodiment, it is preferably 0.3 to 20 wt %, more preferably 0.3 to 10 wt %.

In the transdermal absorption preparation of the present invention, the oleic acid in the transdermal absorption layer is also expected to show the effects of preventing a part of compound A or a pharmaceutically acceptable salt thereof from crystallizing during production or storage and reducing skin irritation during application. The oleic acid can be contained at a high ratio in the transdermal absorption layer. Specifically, the content of the oleic acid in the transdermal absorption layer is preferably 0.1 to 30 wt %, more preferably 0.1 to 25 wt %, further preferably 0.3 to 20 wt %, in 100 wt % of the transdermal absorption layer.

The lower limit of the content of the oleic acid in the transdermal absorption layer is, for example, 0.1 wt %, 0.3 wt %, 0.5 wt %, 1 wt %, 1.5 wt %, 2 wt %, or 3 wt %, in 100 wt % of the transdermal absorption layer, and the upper limit thereof is, for example, 30 wt %, 25 wt %, 20 wt %, 15 wt %, or 10 wt %.

When the above-mentioned organic acid is oleic acid, the content ratio of the levulinic acid and the oleic acid in the transdermal absorption layer is preferably 1:20 to 20:1, more preferably 1:10 to 15:1, further preferably 1:5 to 10:1.

The content of the higher alcohol ester in the transdermal absorption layer is preferably 0.1 to 30 wt %, more preferably 0.5 to 20 wt %, further preferably 1 to 15 wt %, in 100 wt % of the transdermal absorption layer.

The skin permeability of compound A or a pharmaceutically acceptable salt thereof can be improved by blending these additives.

(Ointment Base)

When the transdermal absorption preparation of the present invention is an ointment, the base of the ointment is not particularly limited. For example, oily bases such as fats and oils, waxes (beeswax), hydrocarbons such as paraffin, petrolatum, lanolin, hydrous lanolin, lanolin alcohol, and the like, and the like, or water-soluble bases such as macrogol and the like can be used.

(Transdermal Absorption Layer)

The transdermal absorption layer in the transdermal absorption preparation of the present invention may contain as necessary, in addition to the above-mentioned respective components, other pharmaceutically acceptable additives used in formulating transdermal absorption preparations, as long as no particular problem is caused. While such components are not particularly limited, examples thereof include flavor, colorant, filler, thickener, pH adjuster, emulsifier, suspending agent, and the like.

(Adhesive Layer)

The adhesive layer in the patch preparation of the present invention is formed on at least one surface of the backing film and contains at least (i) compound A or a pharmaceutically acceptable salt thereof and an adhesive base. The adhesive layer preferably further contains (ii) levulinic acid or a pharmaceutically acceptable salt thereof. The adhesive layer may further contain (iii) polyhydric alcohol fatty acid ester or fatty acid amide, and/or (iv) one kind or two or more kinds of additives selected from the group consisting of 2,6-di-tert-butyl-4-methylphenol, sodium thiosulfate, 2-mercaptobenzimidazole, propyl gallate, α-tocopherol, sodium sulfite, and sodium bisulfite.

While the thickness of the adhesive layer is not particularly limited as long as the adhesive layer does not become extremely thick, it is preferably 20 to 600 μm, more preferably 30 to 300 μm, most preferably 50 to 200 μm.

The adhesive layer in the patch preparation of the present invention may contain as necessary, in addition to the above-mentioned respective components, other pharmaceutically acceptable additives used in formulating a patch preparation, as long as no particular problem is caused. Such component is not particularly limited, and examples thereof include flavor, colorant, filler, thickener, and the like.

The flavor is not particularly limited. Examples thereof include dl-menthol, orange oil, peppermint oil, lemon oil, rose oil, and the like. The thickener is not particularly limited. Examples thereof include carboxymethylcellulose, carrageenan, pectin, poly(N-vinylacetamide), poly(N-vinylacetamide-co-acrylic acid), and the like. The pH adjuster is not particularly limited. Examples thereof include citric acid hydrate, glycine, acetic acid, tartaric acid, sodium hydrogen carbonate, lactic acid, and the like. The emulsifier is not particularly limited. Examples thereof include oleyl alcohol, hydroxypropylcellulose, propylene glycol, propylene glycol fatty acid ester, and the like. The suspending agent is not particularly limited. Examples thereof include carmellose sodium, glycerol fatty acid ester, polyoxyethylene hydrogenated castor oil 60, and the like.

(Backing Film)

The patch preparation of the present invention contains a backing film and an adhesive layer formed on at least one surface of the backing film. That is, the backing film has a first surface and a second surface of a sheet-like structure, and forms an adhesive layer on at least the first surface. Where necessary, it may have a release sheet on the surface opposite from the backing film side of the adhesive layer. In addition, the form of the patch preparation may be a sheet with any shape or a rolled form.

(Adhesive Base)

In the patch preparation of the present invention, the formulation of the adhesive layer is not particularly limited. As the adhesive base, for example, acrylic polymer, rubber-based polymer, silicone-based polymer, and the like can be used. One kind or two or more kinds of these polymers can be used in combination.

As the acrylic polymer in the patch preparation of the present invention, an acrylic polymer comprising a unit of alkyl (meth)acrylate as a main constitution unit is preferred. The acrylic polymer containing alkyl (meth)acrylate as a main constitution unit is preferably a copolymer of alkyl (meth)acrylate (the first monomer component) and a vinyl monomer having a functional group capable of being involved in a crosslinking reaction (the second monomer component), or an acrylic polymer wherein a monomer other than these (the third monomer component) is further copolymerized, from the aspects of adhesiveness to human skin, solubility of drug during formulation of a preparation, and the like.

In the present specification, the "(meth)acryl" means both "acryl" and "methacryl".

Examples of the above-mentioned alkyl (meth)acrylate (the first monomer component) include alkyl (meth)acrylate whose alkyl group is a linear, branched chain or cyclic alkyl group having a carbon number of 1 to 18 (e.g., methyl, ethyl, n-propyl, isopropyl, n-butyl, isobutyl, tert-butyl, sec-butyl, n-pentyl, isopentyl, neopentyl, n-hexyl, isohexyl, cyclohexyl, 3-methylpentyl, n-heptyl, cycloheptyl, n-octyl, 2-ethylhexyl, cyclooctyl, n-nonyl, cyclononyl, n-decyl, cyclodecyl, n-undecyl, n-dodecyl, n-tridecyl, n-tetradecyl, isotetradecyl, n-pentadecyl, n-hexadecyl, isohexadecyl, n-octadecyl, isooctadecyl, etc.), and the like, preferably alkyl (meth)acrylate whose alkyl group is a linear, branched chain or cyclic alkyl group having a carbon number of 4 to 18 (e.g., n-butyl, isobutyl, tert-butyl, sec-butyl, n-pentyl, isopentyl, neopentyl, n-hexyl, isohexyl, cyclohexyl, 3-methylpentyl, n-heptyl, cycloheptyl, n-octyl, 2-ethylhexyl, cyclooctyl, n-nonyl, cyclononyl, n-decyl, cyclodecyl, n-undecyl, n-dodecyl, n-tridecyl, etc.). To particularly confer adhesiveness at ambient temperature, use of a monomer component that decreases the glass transition temperature of the polymer is preferred. Thus, alkyl (meth)acrylate wherein the alkyl group is a linear, branched chain or cyclic alkyl group having a carbon number of 4 to 8 (e.g., n-butyl, isobutyl, tert-butyl, sec-butyl, n-pentyl, isopentyl, neopentyl, n-hexyl, isohexyl, cyclohexyl, methylpentyl, n-heptyl, cycloheptyl, n-octyl, 2-ethylhexyl, cyclooctyl and the like) is more preferred, and alkyl (meth)acrylate wherein the alkyl group is n-butyl, 2-ethylhexyl or cyclohexyl is particularly preferred.

Specific, particularly preferable examples of the alkyl (meth)acrylate (the first monomer component) include butyl acrylate, 2-ethylhexyl acrylate, 2-ethylhexyl methacrylate, cyclohexyl acrylate, and cyclohexyl methacrylate. Among these, 2-ethylhexyl acrylate is most preferred. One or more kinds of the alkyl (meth)acrylates (the first monomer component) can be used in combination.

As the above-mentioned vinyl monomer having a functional group capable of being involved in a crosslinking reaction using the aforementioned crosslinking agent (the second monomer component), a vinyl monomer in which the functional group capable of being involved in a crosslinking reaction is a hydroxy group, a carboxy group, a vinyl group or the like can be mentioned, and a vinyl monomer in which the functional group capable of being involved in a crosslinking reaction is a hydroxy group or a carboxy group is preferred. Specific examples of the vinyl monomer (the second monomer component) include hydroxyethyl (meth) acrylate, hydroxypropyl (meth)acrylate, (meth)acrylic acid, itaconic acid, maleic acid, maleic anhydride, methaconic acid, citraconic acid, glutaconic acid, and the like. Among these, acrylic acid, methacrylic acid and hydroxyethyl acrylate are preferred, and acrylic acid is most preferred, since they are easily available. One or more kinds of the vinyl monomers (the second monomer component) can be used in combination.

In addition, the aforementioned other monomer (the third monomer component) is mainly used for adjusting the cohesive force of the adhesive layer, adjusting solubility and/or releasability of a drug (compound A or a pharmaceutically acceptable salt thereof) and the like. Examples of such other monomer (the third monomer component) include vinyl esters such as vinyl acetate, vinyl propionate, and the like; vinyl ethers such as methyl vinyl ether, ethyl vinyl ether, and the like; vinyl amides such as N-vinyl-2-pyrrolidone, N-vinyl caprolactam, and the like; alkoxy group-containing monomers such as methoxyethyl (meth) acrylate, ethoxyethyl (meth)acrylate, tetrahydrofurfuryl (meth)acrylate, and the like; hydroxy group-containing monomers such as hydroxypropyl (meth)acrylate, α-hydroxymethyl acrylate, and the like (such hydroxy group-containing monomer is used as the third monomer component and is not involved in a crosslinking reaction); amide group-containing (meth)acrylic acid derivatives such as (meth)acrylamide, dimethyl(meth)acrylamide, N-butyl (meth)acrylamide, N-methylol(meth)acrylamide, and the like; aminoalkyl (meth)acrylates such as aminoethyl (meth) acrylate, dimethylaminoethyl (meth)acrylate, tert-butylaminoethyl (meth)acrylate, and the like; alkoxyalkylene glycol (meth)acrylates such as methoxyethylene glycol (meth)acrylate, methoxydiethylene glycol (meth)acrylate, methoxypolyethylene glycol (meth)acrylate, methoxypolypropylene glycol (meth)acrylate, and the like; (meth)acrylonitriles; sulfo group-containing monomers such as styrenesulfonic acid, allylsulfonic acid, sulfopropyl (meth)acrylate, (meth) acryloyloxy naphthalene sulfonic acid, acrylamide methylsulfonic acid, and the like; vinyl group-containing monomers such as vinylpiperidone, vinylpyrimidine, vinylpiperazine, vinylpyrrole, vinylimidazole, vinyloxazole, vinylmorpholine, and the like, and the like. Among these, vinyl esters (e.g., vinyl acetate) and vinyl amides (e.g., N-vinyl-2-pyrrolidone) are preferred. One kind or two or more kinds of such other monomers (the third monomer component) can be used in combination.

When the acrylic polymer in the patch preparation of the present invention is a copolymer of alkyl (meth)acrylate (the first monomer component) and a vinyl monomer having a functional group capable of being involved in a crosslinking reaction (the second monomer component), the copolymerization ratio (first monomer component/second monomer component) is preferably 85 to 99 wt %/1 to 15 wt %, more preferably 90 to 99 wt %/1 to 10 wt %.

When the acrylic polymer in the patch preparation of the present invention is a copolymer of alkyl (meth)acrylate (the first monomer component), a vinyl monomer having a functional group capable of being involved in a crosslinking reaction (the second monomer component), and a monomer other than these (the third monomer component), the copolymerization ratio (first monomer component/second monomer component/third monomer component) is preferably 35 to 94 wt %/1 to 15 wt %/5 to 50 wt %, more preferably 50 to 89 wt %/1 to 10 wt %/10 to 40 wt %.

While the polymerization reaction using the aforementioned respective monomer components may be performed by a method known per se and is not particularly limited, for example, a method including reacting the aforementioned monomer in a solvent (e.g., ethyl acetate and the like) in the presence of a polymerization initiator (e.g., benzoyl peroxide, azobisisobutyronitrile and the like) at 50 to 70° C. for 5 to 48 hr can be mentioned.

The acrylic polymer in the patch preparation of the present invention is preferably a 2-ethylhexyl acrylate/acrylic acid/N-vinyl-2-pyrrolidone copolymer, a 2-ethylhexyl acrylate/2-hydroxyethyl acrylate/vinyl acetate copolymer, a 2-ethylhexyl acrylate/acrylic acid copolymer and the like, particularly preferably a 2-ethylhexyl acrylate/acrylic acid/N-vinyl-2-pyrrolidone copolymer.

While the glass transition temperature of the acrylic polymer in the patch preparation of the present invention also varies depending on the copolymer composition, it is preferably −100 to −10° C., more preferably −90 to −20° C., from the aspect of adhesiveness of a patch preparation. The glass transition temperature is a measured value by a differential scanning calorimeter.

Examples of the rubber-based polymer in the patch preparation of the present invention include styrene-isoprene-styrene block copolymer, isoprene rubber, polyisobutylene, styrene-butadiene-styrene block copolymer, styrene-ethylene-butylene-styrene block copolymer, styrene-ethylene-propylene-styrene block copolymer, styrene-butadiene rubber, and the like. Among these, styrene-isoprene-styrene block copolymer and polyisobutylene are preferred, and styrene-isoprene-styrene block copolymer is more preferred. One kind or two or more kinds of the rubber-based polymers can be used in combination.

As the silicone-based polymer in the patch preparation of the present invention, for example, one containing polyorganosiloxane such as silicone rubber, dimethylsiloxane base, diphenylsiloxane base, polydimethyl siloxane, or the like as a main component, and containing a tackifier such as MQ resin or the like, and the like can be used. One kind or two or more kinds of the silicone-based polymers can be used in combination.

In the patch preparation of the present invention, the content of the adhesive base in the adhesive layer is preferably 30 to 80 wt %, more preferably 40 to 70 wt %, in 100 wt % of the adhesive layer.

(Release Liner)

In the patch preparation of the present invention, the surface on the side opposite to the backing film side of the adhesive layer (adhesion surface to the skin) is preferably laminated with a release liner until actual use of the preparation. The release liner is not particularly limited, and a known release liner can be used. Specific examples thereof include a release liner wherein a release treating agent layer comprised of the release treating agent is formed on the surface of a substrate for a release liner, a plastic film having high releasability by itself, a release liner having a constitution wherein a release layer comprised of the aforementioned plastic film material having high releasability is formed on the surface of a substrate for a release liner and the like. The release surface of the release liner may be only one surface or both surfaces of the substrate.

In such release liner, the release treating agent is not particularly limited and, for example, release agents such as a long chain alkyl group-containing polymer, a silicone-based polymer (silicone-based release agent), a fluorine-based polymer (fluorine-based release agent) and the like can be mentioned. Examples of the substrate for a release liner include plastic films such as a polyethylene terephthalate (PET) film, a polyimide film, a polypropylene film, a polyethylene film, a polycarbonate film, a polyester (excluding PET) film and the like, and metallized plastic films wherein a metal is evaporated on these films; papers such as Japanese paper, Western paper, craft paper, glassine paper, fine paper and the like; a substrate made of a fibrous material such as non-woven fabric, cloth and the like; a metal foil and the like.

As the plastic film having high releasability by itself, polyethylene (low density polyethylene, linear low density polyethylene etc.), polypropylene, ethylene-α-olefin copolymers (block copolymer or random copolymer) such as ethylene-propylene copolymer and the like, a polyolefin-based film made of a polyolefin-based resin comprised of a mixture of these; Teflon (registered trade mark) film and the like can be used.

The release layer formed on the surface of the aforementioned substrate for a release liner can be formed by laminating or coating the aforementioned plastic film material having high releasability on the aforementioned substrate for a release liner.

While the thickness (total thickness) of the release liner is not particularly limited, it is generally not more than 200 μm, preferably 25 to 100 μm.

(Evaluation Method of the Patch Preparation of the Present Invention)

The skin adhesiveness of the patch preparation of the present invention can be evaluated using a test method such as tack strength test, tensile test, peeling test (JIS Z 0237: 2009, JIS K 6854), or the like. For example, In the tack strength test, for example, when the patch preparation of the present invention is peeled off from the liner and the thumb is pressed against the plaster surface and peeled off for evaluation in a sensory test, an appropriate adhesiveness when peeling off the thumb is preferred.

As the evaluation of the skin irritation of the patch preparation of the present invention, for example, when the patch preparation of the present invention is adhered to the normal skin on the back of a rabbit, and the skin reaction is visually observed 24 hr after the administration (30 min after unblocking and specimen removal), further 48 hr and 72 hr after administration, the observation score according to the criteria of the Draize method is preferably not more than 2.

As the criteria of the Draize method, according to the scores shown below, an average individual score of skin response of each animal (observation score=(total of erythema and crust formation+edema formation)/number of observation points) is used.

(Criteria of Draize Method)

erythema and crust formation

0: no erythema
1: very slight erythema
2: clear erythema
3: moderate to intense erythema
4: strong erythema to crust formation edema formation 0: no edema
1: very slight edema
2: clear edema
3: moderate edema
4: strong edema (Production Method of the Transdermal Absorption Preparation of the Present Invention)

The transdermal absorption preparation of the present invention can be produced using a pharmaceutically acceptable additive and according to a known method.

[1. Production Method of Ointment of the Present Invention]

The production method of the ointment of the present invention is not particularly limited, and the ointment can be produced by a generally-known method. For example, it can be produced by the following production method.

An ointment base, compound A or a pharmaceutically acceptable salt thereof, additive A group, and additive B group, and other additives where necessary are added to a suitable solvent, the mixture is sufficiently mixed until homogeneous to form a semi-solid ointment. Examples of the solvent include water, glycerol, propylene glycol, polyethylene glycol, 1,3-butylene glycol, ethanol, isopropanol, and the like.

In order to produce an oily ointment, an oily base such as fats and oils, waxes, hydrocarbons such as paraffin and the like, or the like is melted by heating, compound A or a pharmaceutically acceptable salt thereof, additive A group, and additive B group are added, blended and dissolved or dispersed, and the whole is mixed and kneaded until it becomes homogeneous. In order to produce a water-soluble ointment, generally, a water-soluble base such as macrogol or the like is melted by heating, compound A or a pharmaceutically acceptable salt thereof, additive A group, and additive B group are added, and the whole is mixed and kneaded until it becomes homogeneous.

To be specific, for example, to compound A or a pharmaceutically acceptable salt thereof are added levulinic acid or a pharmaceutically acceptable salt thereof, and additive B group, and, where necessary, organic liquid components and other additives, as well as higher alcohol such as cetanol, stearyl alcohol, or the like, higher fatty acid or ester thereof such as myristic acid, lauric acid, palmitic acid, stearic acid, linoleic acid, or the like, wax such as purified lanolin, whale wax, or the like, surfactant such as sorbitan fatty acid ester, sucrose fatty acid ester, or the like, hydrocarbon such as hydrophilic petrolatum, liquid paraffin, plastibase, or the like, and the like, and they are mixed under heating, maintained at 50 to 100° C. and, after the whole components have formed a clear solution, uniformly blended with a homomixer. Thereafter, an ointment can be obtained by cooling and stirring while allowing to cool.

[2. Production Method of the Patch Preparation of the Present Invention]

While the production method of the patch preparation of the present invention is not particularly limited, it can be produced by, for example, the following production method.

An adhesive base containing an acrylic polymer, compound A or a pharmaceutically acceptable salt thereof, levulinic acid or a pharmaceutically acceptable salt thereof, and additive B group are added, together with an organic liquid component and other additives as necessary, to a suitable solvent and the mixture is sufficiently mixed until it becomes homogeneous. Examples of the solvent include ethyl acetate, toluene, hexane, 2-propanol, methanol, ethanol, water, and the like. When a crosslinking agent is added, it is added to the mixture and the mixture is sufficiently mixed. Where necessary, a solvent may be added along with a crosslinking agent and they are mixed.

Then, the obtained mixture is applied to one surface of the backing film or a release treating surface of the release liner, and dried to form an adhesive layer. The aforementioned application can be performed by, for example, casting, printing and other techniques known per se to those of ordinary skill in the art. Thereafter, a release liner or backing film is adhered to the adhesive layer to form a laminate. When a crosslinking treatment is performed, the release liner or backing film is adhered to the adhesive layer, and they are left standing generally at 60 to 90° C., preferably 60 to 70° C., for 24 to 48 hr to promote the crosslinking reaction, whereby a crosslinked adhesive layer is formed.

(Dose of the Transdermal Absorption Preparation of the Present Invention)

While the dose of the transdermal absorption preparation of the present invention varies depending on the age, body weight, symptom and the like of the patient, it is generally 0.1 to 500 mg, preferably 1 to 100 mg, more preferably 2 to 50 mg, further preferably 2 to 35 mg, per day for adults generally as a compound A conversion value.

When the transdermal absorption preparation of the present invention is a patch preparation, the size of the patch preparation of the present invention is generally 2 to 100 $cm^2$, preferably 2 to 70 $cm^2$, more preferably 4 to 50 $cm^2$. The patch preparation of the present invention is generally changed to a new one at a frequency of 3 times/day to once/week, preferably once/day to once/week, more preferably once/day.

(Concomitant Drug)

In the transdermal absorption preparation of the present invention, compound A or a pharmaceutically acceptable salt thereof can be used in combination with other drug (hereinafter sometimes to be referred to as "concomitant drug") as long as the efficacy thereof is not impaired. In this case, the administration period is not limited, and these can be administered simultaneously to the subject of administration, or may be administered at different times. In addition, it is also possible to administer a single preparation containing compound A or a pharmaceutically acceptable salt thereof and a concomitant drug in combination. Examples of the concomitant drug include levodopa and existing therapeutic drugs for Parkinson's disease. Specific examples of existing therapeutic drug for Parkinson's disease include, but are not limited to, dopamine agonists (e.g., bromocriptine, pergolide, talipexole, cabergoline, pramipexole, ropinirole, rotigotine, etc.), monoamine oxidase B (MAOB) inhibitors (e.g., selegiline, rasagiline, safinamide), catechol O-methyl group transferase (COMT) inhibitors (e.g., entacapone), amantadine, apomorphine, istradefylline, anticholinergic agents (e.g., biperiden, trihexyphenidyl, profenamine, mazaticol), tiapuride, droxidopa, carbidopa, zonisamide, and the like.

EXAMPLE

The present invention is explained in detail in the following by referring to Examples and Experimental Examples, which are not to be construed as limitative. In the following sentences, "parts" and "%" all mean parts by weight and wt %.

[Preparation of Acrylic Polymer A]

Under an inert gas atmosphere, 2-ethylhexyl acrylate (55 parts), N-vinyl-2-pyrrolidone (40 parts), N-(2-hydroxyethyl) acrylamide (5 parts), and azobisisobutyronitrile (0.2 parts) were subjected to solution polymerization in ethyl acetate at 60° C. to prepare an acrylic polymer (acrylic polymer A) solution.

[Preparation of Acrylic Polymer B]

Under an inert gas atmosphere, 2-ethylhexyl acrylate (75 parts), N-vinyl-2-pyrrolidone (22 parts), acrylic acid (3 parts) and azobisisobutyronitrile (0.2 parts) were subjected to solution polymerization in ethyl acetate at 60° C. to give an acrylic polymer (acrylic polymer B) solution.

<Evaluation Test>

In order to increase the content of compound A in the patch preparation (tape preparation), it is preferable to add an additive with high drug solubility. Therefore, the saturation solubility of compound A was measured using various additives having different HLB values. The results of the measurements are shown in Table 1. In addition, for the additives having high saturation solubility in Table 1 (that is, lactic acid, levulinic acid, and oleic acid), liquids in which various other additives were combined were prepared, and the skin permeation amount of compound A was measured for each liquid. The results are shown in Table 2.

Experimental Example 1: Saturation Solubility Measurement

Various additives were weighed into a vial, compound A was added until it was no longer dissolved, and the mixture was stirred overnight at room temperature. The mixture was filtered using a 0.45 μm PTFE filter and the concentration of compound A in the filtrate was quantified by high performance liquid chromatography (ODS column, UV detector). When the concentration of compound A exceeded 20%, the addition of compound A was stopped.

Experimental Example 2: Skin Permeability Test of Solution

The skin removed from a miniature pig was attached to a skin permeation experimental cell (effective area 3 mmφ, receptor solution amount 1.25 mL) such that the corium layer side became the receptor layer, a saturated solution of compound A (5 μL) with various additives was added, and a skin permeability test was performed for 24 hr under the condition of receptor solution temperature of 32±1° C. A degassed PBS(−) solution (phosphate buffered saline) was used as the receptor solution. After 24 hr, the receptor solution was sampled, and the concentration of the permeated compound A was quantified by high performance liquid chromatography (ODS column, UV detector).

TABLE 1

Saturation solubility (%) of compound A (tandospirone) with each additive

| No. | additive | saturation solubility (%) |
|---|---|---|
| 1 | lactic acid *1 | not less than 20 |
| 2 | levulinic acid *1 | not less than 20 |
| 3 | dipropylene glycol | 1.6 |
| 4 | polysorbate 20 | 1.4 |
| 5 | polysorbate 80 | 1.4 |
| 6 | N-methyl-2-pyrrolidone | 15.4 |
| 7 | sorbitan monolaurate *2 | 2.3 |
| 8 | lauromacrogol (4) | 2.0 |
| 9 | propylene glycol fatty acid ester (C8) | 5.0 |
| 10 | diisopropyl adipate | 2.0 |
| 11 | propylene glycol fatty acid ester (C12) | 5.9 |
| 12 | oleic acid *1 | not less than 20 |
| 13 | propylene glycol fatty acid diester (C8) | 1.3 |
| 14 | oleyl alcohol | 1.0 |
| 15 | isopropyl myristate | 0.6 |

*1: Drug addition was stopped when the solubility exceeded 20%.

*2: The saturation solubility was measured as a mixed solution of isopropyl myristate/sorbitan monolaurate = 50/50 because viscosity is high when used alone.

TABLE 2

Comparison of skin permeation amount of compound A (tandospirone) when combined with additives

| | constituent component of liquid* | cumulative permeation amount (μg/24 h) |
|---|---|---|
| 1 | IPM/lactic acid/PGMC/none | 2.4 |
| 2 | IPM/lactic acid/PGMC/N-methyl-2-pyrrolidone | 3.9 |
| 3 | IPM/lactic acid/PGMC/lauromacrogol (4) | 4.4 |
| 4 | IPM/lactic acid/PGMC/polysorbate 80 | 2.2 |
| 5 | IPM/lactic acid/PGMC/diisopropyl adipate | 1.8 |
| 6 | IPM/lactic acid/PGMC/sorbitan monolaurate | 1.6 |
| 7 | IPM/lactic acid/PGML/none | 5.2 |
| 8 | IPM/lactic acid/PGML/N-methyl-2-pyrrolidone | 12.9 |
| 9 | IPM/lactic acid/PGML/lauromacrogol (4) | 9.8 |
| 10 | IPM/lactic acid/PGML/polysorbate 80 | 6.6 |

TABLE 2-continued

Comparison of skin permeation amount of compound A (tandospirone) when combined with additives

| | constituent component of liquid* | cumulative permeation amount (μg/24 h) |
|---|---|---|
| 11 | IPM/lactic acid/PGML/diisopropyl adipate | 2.3 |
| 12 | IPM/lactic acid/PGML/sorbitan monolaurate | 14.8 |
| 13 | IPM/levulinic acid/PGMC/none | 28.3 |
| 14 | IPM/levulinic acid/PGMC/N-methyl-2-pyrrolidone | 19.6 |
| 15 | IPM/levulinic acid/PGMC/lauromacrogol (4) | 37.4 |
| 16 | IPM/levulinic acid/PGMC/polysorbate 80 | 10.0 |
| 17 | IPM/levulinic acid/PGMC/diisopropyl adipate | 10.8 |
| 18 | IPM/levulinic acid/PGMC/sorbitan monolaurate | 19.7 |
| 19 | IPM/levulinic acid/PGML/none | 15.0 |
| 20 | IPM/levulinic acid/PGML/N-methyl-2-pyrrolidone | 26.7 |
| 21 | IPM/levulinic acid/PGML/lauromacrogol (4) | 33.8 |
| 22 | IPM/levulinic acid/PGML/polysorbate 80 | 8.5 |
| 23 | IPM/levulinic acid/PGML/diisopropyl adipate | 9.3 |
| 24 | IPM/levulinic acid/PGML/sorbitan monolaurate | 10.6 |
| 25 | IPM/oleic acid/PGMC/none | |
| 26 | IPM/oleic acid/PGMC/N-methyl-2-pyrrolidone | 9.1 |
| 27 | IPM/oleic acid/PGMC/lauromacrogol (4) | 12.1 |
| 28 | IPM/oleic acid/PGMC/polysorbate 80 | 13.2 |
| 29 | IPM/oleic acid/PGMC/diisopropyl adipate | 7.5 |
| 30 | IPM/oleic acid/PGMC/sorbitan monolaurate | 8.5 |
| 31 | IPM/oleic acid/PGML/none | 8.4 |
| 32 | IPM/oleic acid/PGML/N-methyl-2-pyrrolidone | 9.4 |
| 33 | IPM/oleic acid/PGML/lauromacrogol (4) | 14.6 |
| 34 | IPM/oleic acid/PGML/polysorbate 80 | 12.4 |
| 35 | IPM/oleic acid/PGML/diisopropyl adipate | 10.6 |
| 36 | IPM/oleic acid/PGML/sorbitan monolaurate | 10.6 |
| 37 | IPM | 6.7 |

*IPM: isopropyl myristate, PGMC: propylene glycol monocaprylate, PGML: propylene glycol monolaurate
*As the mixing ratio of respective constituent components, additives other than IPM were blended by 10 wt %, and IPM was blended to the total of 100 wt %.

According to Table 1, it was found that lactic acid, levulinic acid, and oleic acid, which are organic acids, show high saturation solubility of compound A among various additives.

As shown in Table 2, liquids consisting of 3 or 4 kinds of combinations of lactic acid, levulinic acid, and oleic acid, which showed high saturation solubility of compound A in Table 1, with various additives were prepared. Then, the skin permeation amount of compound A was measured for respective liquids in which compound A was saturated. The following points are clear from the measurement results.

(1) It was found that the combinations Nos. 13 to 24 containing levulinic acid showed relatively high skin permeability of compound A, compared with combinations Nos. 1 to 12 containing lactic acid and combinations Nos. 25 to 36 containing oleic acid. It was an unexpected result that, among the organic acids (lactic acid, levulinic acid, and oleic acid) showing equivalent high saturation solubility, remarkably superior skin permeability of compound A was observed in the combinations containing levulinic acid.

(2) In particular, it was found that, in the combinations of levulinic acid, polyhydric alcohol fatty acid ester, and TO surfactant, high skin permeability of compound A can be obtained, and among them, high skin permeability of compound A was obtained in the combinations of isopropyl myristate, levulinic acid, propylene glycol fatty acid ester, and lauromacrogol (No. 15 and No. 21).

Example 1

Acrylic polymer A (50.0 parts), compound A (20.0 parts), isopropyl myristate (hereinafter to be referred to as "IPM") (20.0 parts), propylene glycol monocaprylate (hereinafter to be referred to as "PGMC") (5.0 parts), and levulinic acid (5.0 parts) were dissolved in appropriate amounts of ethyl acetate and toluene, and the solution was sufficiently mixed until it became homogeneous. The base concentration was adjusted to 20 wt % with toluene and the mixture was sufficiently mixed and stirred until it became homogeneous to give a coating solution. The obtained coating solution was applied to a release-treated surface of a release liner, which was a 75 μm-thick polyethylene terephthalate (hereinafter to be referred to as "PET") film subjected to a release treatment with a silicone-based release agent, such that the thickness of the plaster after drying was about 150 μm, and dried to form an adhesive layer. The adhesive surface of the adhesive layer thus formed was adhered to a nonwoven fabric side of a laminate film of a PET film and a PET nonwoven fabric to give a laminate, whereby the patch preparation of Example 1 was obtained.

The above-mentioned base concentration (wt %) refers to a value (wt %) obtained by subtracting the weight (g) of ethyl acetate from the weight (g) of the coating solution, dividing the obtained value by the weight (g) of the coating solution and multiplying the obtained value by 100.

Example 2

In the same manner as in Example 1 except that IPM (17.5 parts) and levulinic acid (7.5 parts) were used, the patch preparation of Example 2 was obtained.

Example 3

In the same manner as in Example 1 except that IPM (15.0 parts) and levulinic acid (10.0 parts) were used, the patch preparation of Example 3 was obtained.

Example 4

Acrylic polymer C (MAS683, CosMED Pharmaceutical Co., Ltd.) (60.0 parts), compound A (5.0 parts), IPM (30.0 parts), and levulinic acid (5.0 parts) were dissolved in an appropriate amount of ethyl acetate and added, and the solution was sufficiently mixed until it became homogeneous to give a coating solution. The obtained coating solution was applied to a PET film as a backing film such that the thickness of the plaster after drying was about 100 μm, and dried to form an adhesive layer. The adhesive layer thus formed was adhered to a release liner to give the patch preparation of Example 4.

Example 5

In the same manner as in Example 4 except that IPM (25.0 parts) and levulinic acid (10.0 parts) were used, the patch preparation of Example 5 was obtained.

Example 6

In the same manner as in Example 4 except that acrylic polymer C (50.0 parts), IPM (15.0 parts), and levulinic acid (10.0 parts) were used, 2,6-di-tert-butyl-4-methylphenol (5.0 parts) was added, and sodium thiosulfate (as anhydrate) (5.0 parts) was further dissolved in an appropriate amount of water for injection and added, the patch preparation of Example 6 was obtained.

Example 6a

In the same manner as in Example 4 except that IPM (12.5 parts) was used and oleic acid (1.5 parts), propylene glycol monolaurate (hereinafter to be referred to as "PGML") (10.0 parts), lauromacrogol (5.0 parts), and 2,6-di-tert-butyl-4-methylphenol (1.0 part) were added, the patch preparation of Example 6a was obtained.

Example 6b

In the same manner as in Example 6a except that IPM (9.0 parts) and oleic acid (5.0 parts) were used, the patch preparation of Example 6b was obtained.

Comparative Example 1

In the same manner as in Example 1 except that levulinic acid was not used and lactic acid (5.0 parts) was used, the patch preparation of Comparative Example 1 was obtained.

Comparative Example 2

In the same manner as in Comparative Example 1 except that IPM (17.5 parts) and lactic acid (7.5 parts) were used, the patch preparation of Comparative Example 2 was obtained.

Comparative Example 3

In the same manner as in Comparative Example 1 except that IPM (15.0 parts) and lactic acid (10.0 parts) were used, the patch preparation of Comparative Example 3 was obtained.

Comparative Example 4

In the same manner as in Example 4 except that levulinic acid was not used and IPM (35.0 parts) was added, the patch preparation of Comparative Example 4 was obtained.

Comparative Example 5

In the same manner as in Example 4 except that levulinic acid was not used and acetic acid (5.0 parts) was added, the patch preparation of Comparative Example 5 was obtained.

Comparative Example 6

In the same manner as in Comparative Example 5 except that acetic acid was not used and lactic acid (5.0 parts) was added, the patch preparation of Comparative Example 6 was obtained.

Comparative Example 6a

In the same manner as in Comparative Example 4 except that IPM (34.0 parts) was used and 2,6-di-tert-butyl-4-methylphenol (1.0 part) was added, the patch preparation of Comparative Example 6a was obtained.

<Evaluation Test>

The patch preparations produced in the above-mentioned Examples and Comparative Examples were subjected to the following test. The results are shown in Table 3, Table 4-1, and Table 4-2.

Experimental Example 3: Skin Permeability Test 1 of Preparation—Flow Cell Method A patch preparation was adhered to the stratum corneum layer side of the skin removed from a hairless mouse, and attached to a flow cell (effective area 6 mmφ) for skin permeation experiments such that the corium layer side became the receptor layer. A skin permeation experiment was performed for 24 hr under the conditions of flow rate 2.5 mL/h and receptor solution temperature 32±1° C. A degassed PBS(−) solution (phosphate buffered saline) was used as the receptor solution. The receptor solution was sampled over time, and the concentration of the permeated compound A was quantified by high performance liquid chromatography (ODS column, UV detector).

Experimental Example 4: Skin Permeability Test 2 of Preparation—Plate Method

A patch preparation was adhered to the stratum corneum layer side of the skin removed from a hairless mouse, and attached to a plate cell (effective area 8 mmφ, receptor solution amount 1.4 mL) for skin permeation experiments such that the corium layer side became the receptor layer. A skin permeation experiment was performed for 24 hr under the condition of receptor solution temperature 32±1° C. A degassed PBS(−) solution (phosphate buffered saline) was used as the receptor solution. The receptor solution was sampled 24 hr later, and the concentration of the permeated compound A was quantified by high performance liquid chromatography (ODS column, UV detector).

TABLE 3

Skin permeability test of patch preparation (flow cell method)

| | acrylic polymer A (parts) | compound A (parts) | IPM (parts) | PGMC (parts) | levulinic acid (parts) | lactic acid (parts) | skin permeability of compound A: cumulative permeation amount (μg/cm$^2$/24 h) | maximum permeation rate (μg/cm$^2$/h) |
|---|---|---|---|---|---|---|---|---|
| Example 1 | 50 | 20 | 20 | 5 | 5 | — | 835 | 45.7 |
| Example 2 | 50 | 20 | 17.5 | 5 | 7.5 | — | 1020 | 54.0 |

TABLE 3-continued

Skin permeability test of patch preparation (flow cell method)

| | acrylic polymer A (parts) | compound A (parts) | IPM (parts) | PGMC (parts) | levulinic acid (parts) | lactic acid (parts) | skin permeability of compound A: cumulative permeation amount (μg/$cm^2$/24 h) | skin permeability of compound A: maximum permeation rate (μg/$cm^2$/h) |
|---|---|---|---|---|---|---|---|---|
| Example 3 | 50 | 20 | 15 | 5 | 10 | — | 1036 | 52.7 |
| Comparative Example 1 | 50 | 20 | 20 | 5 | — | 5 | 524 | 26.0 |
| Comparative Example 2 | 50 | 20 | 17.5 | 5 | — | 7.5 | 359 | 20.6 |
| Comparative Example 3 | 50 | 20 | 15 | 5 | — | 10 | 199 | 12.9 |

TABLE 4-1

Skin permeability test of patch preparation (plate method)

| | acrylic polymer C | compound A (parts) | IPM (parts) | levulinic acid (parts) | acetic acid (parts) | lactic acid (parts) | 2,6-di-tert-butyl-4-methylphenol (parts) | sodium thiosulfate (anhydrous) (parts) | skin permeability of compound A: cumulative permeation amount (μg/$cm^2$/24 h) | skin permeability of compound A: maximum permeation rate (μg/$cm^2$/h) |
|---|---|---|---|---|---|---|---|---|---|---|
| Example 4 | 60 | 5 | 30 | 5 | — | — | — | — | 653 | 27.2 |
| Example 5 | 60 | 5 | 25 | 10 | — | — | — | — | 487 | 20.3 |
| Example 6 | 60 | 5 | 15 | 20 | — | — | 5 | 5 | 552 | 23.0 |
| Comparative Example 4 | 60 | 5 | 35 | — | — | — | — | — | 365 | 15.2 |
| Comparative Example 5 | 60 | 5 | 30 | — | 5 | — | — | — | 376 | 15.7 |
| Comparative Example 6 | 60 | 5 | 30 | — | — | 5 | | — | 282 | 11.8 |

TABLE 4-2

Skin permeability test of patch preparation (plate method)

| | acrylic polymer C | compound A (parts) | IPM (parts) | levulinic acid (parts) | oleic acid (parts) | PGML (parts) | lauromacrogol (parts) | 2,6-di-tert-butyl-4-methylphenol (parts) | skin permeability of compound A: cumulative permeation amount (μg/$cm^2$/24 h) | skin permeability of compound A: maximum permeation rate (μg/$cm^2$/h) |
|---|---|---|---|---|---|---|---|---|---|---|
| Example 6a | 60 | 5 | 12.5 | 5 | 1.5 | 10 | 5 | 1 | 436 | 18.2 |
| Example 6b | 60 | 5 | 9 | 5 | 5 | 10 | 5 | 1 | 458 | 19.1 |

TABLE 4-2-continued

Skin permeability test of patch preparation (plate method)

| | acrylic polymer C | compound A (parts) | IPM (parts) | levulinic acid (parts) | oleic acid (parts) | PGML (parts) | lauro-macrogol (parts) | 2,6-di-tert-butyl-4-methyl-phenol (parts) | skin permeability of compound A: cumulative permeation amount (μg/cm²/24 h) | skin permeability of compound A: maximum permeation rate (μg/cm²/h) |
|---|---|---|---|---|---|---|---|---|---|---|
| Comparative Example 6a | 60 | 5 | 34 | — | — | — | — | 1 | 389 | 16.2 |

From the results in Table 3, the following points are clear.

(1) Compared with Comparative Examples 1 to 3 containing lactic acid in the adhesive layer, the skin permeability of compound A was remarkably improved and the maximum permeation rate was not less than 45 $\mu g/cm^2/h$ in Examples 1 to 3 containing levulinic acid.

(2) In Comparative Examples 1 to 3, when the lactic acid content was increased, the skin permeability decreased, whereas in Examples 1 to 3, when the levulinic acid content was increased, the skin permeability was improved in an addition amount-dependent manner.

In addition, from the results in Table 4-1, the following points are clear.

(1) Compared with Comparative Example 4 not containing an organic acid in the adhesive layer, the cumulative permeation amount and the maximum permeation rate were improved by about 1.5 times, and the skin permeability of compound A was improved in Examples 4 to 6 containing levulinic acid.

(2) On the other hand, in Comparative Examples 5 and 6 containing acetic acid or lactic acid, the skin permeability of Compound A was not remarkably improved compared with Comparative Example 4 not containing an organic acid.

From the results in Table 4-2, the following points are clear.

(1) In Examples 6a and 6b containing levulinic acid, oleic acid, PGML, and lauromacrogol, it was found that the skin permeability of compound A was improved compared with Comparative Example 6a not containing an organic acid.

Example 7

In the same manner as in Example 1 except that PGMC was not used, acrylic polymer A (50.0 parts), compound A (20.0 parts), IPM (25.0 parts), and levulinic acid (5.0 parts) were used, and the coating solution was applied to a plaster thickness of about 100 μm, the patch preparation of Example 7 was obtained.

Example 8

In the same manner as in Example 1 except that IPM (20.0 parts) was used, PGMC (5.0 parts) was added, and the coating solution was applied to a plaster thickness of about 100 μm, the patch preparation of Example 8 was obtained.

Comparative Example 7

In the same manner as in Example 1 except that PGMC and levulinic acid were not used, IPM (30.0 parts) was used, and the coating solution was applied to a plaster thickness of about 100 μm, the patch preparation of Comparative Example 7 was obtained.

Comparative Example 8

In the same manner as in Example 1 except that levulinic acid was not used, IPM (25.0 parts) was used, and the coating solution was applied to a plaster thickness of about 100 μm, the patch preparation of Comparative Example 8 was obtained.

<Evaluation Test>

The preparations produced in the above-mentioned Examples and Comparative Examples were subjected to the evaluation of Experimental Example 3. The results are shown in Table 5.

TABLE 5 synergistic effect on skin permeability by combination of levulinic acid and polyhydric alcohol fatty acid ester

| | acrylic polymer A (parts) | compound A (parts) | IPM (parts) | PGMC (parts) | levulinic acid (parts) | skin permeability of compound A: cumulative permeation amount (μg/cm²/24 h) | skin permeability of compound A: maximum permeation rate (μg/cm²/h) |
|---|---|---|---|---|---|---|---|
| Example 7 | 50.0 | 20.0 | 25.0 | — | 5.0 | 884.0 | 54.7 |
| Example 8 | 50.0 | 20.0 | 20.0 | 5.0 | 5.0 | 1007.0 | 58.7 |
| Comparative Example 7 | 50.0 | 20.0 | 30.0 | — | — | 112.0 | 5.8 |

TABLE 5-continued

| synergistic effect on skin permeability by combination of levulinic acid and polyhydric alcohol fatty acid ester | | | | | | | |
|---|---|---|---|---|---|---|---|
| | | | | | | skin permeability of compound A | |
| | acrylic polymer A (parts) | compound A (parts) | IPM (parts) | PGMC (parts) | levulinic acid (parts) | cumulative permeation amount ($\mu g/cm^2/24$ h) | maximum permeation rate ($\mu g/cm^2/h$) |
| Comparative Example 8 | 50.0 | 20.0 | 25.0 | 5.0 | — | 86.0 | 4.5 |

From the results in Table 5, the following points are clear.

(1) Compared with Comparative Example 7 not containing the additive A group in the adhesive layer, in Comparative Example 8 containing only the polyhydric alcohol fatty acid ester PGMC, improvement in the skin permeability of compound A was hardly observed. In contrast, a remarkable improvement in the skin permeability of compound A was observed in Example 7 containing levulinic acid. Furthermore, in Example 8, it was found that the skin permeability of compound A was synergistically improved by combining levulinic acid with PGMC (to be additive group A) which showed almost no promoting effect on the skin permeability of compound A when used alone.

Example 9

Acrylic polymer B (45.0 parts), compound A (5.5 parts), IPM (31.7 parts), PGML (10.0 parts), levulinic acid (5.0 parts), lauromacrogol (1.5 parts), 2,6-di-tert-butyl-4-methylphenol (1.0 part), and sodium thiosulfate (as anhydrate) dissolved in an appropriate amount of water for injection (0.08 parts) were dissolved in an appropriate amount of ethyl acetate and toluene, and the solution was sufficiently mixed until it became homogeneous. As a crosslinking agent, aluminum ethylacetoacetate diisopropylate (hereinafter "ALCH".) (0.1 parts) was dissolved in an appropriate amount of ethyl acetate and acetylacetone and added thereto, and the solution was sufficiently mixed until it became homogeneous to give a coating solution. The obtained coating solution was applied in the same manner as in Example 1 except that the thickness of the plaster was about 100 μm, and dried to form an adhesive layer. The adhesive layer was adhered to a backing film to produce a laminate. Thereafter, it was allowed to stand at 70° C. for 48 hr, and a crosslinked adhesive layer was prepared to obtain the patch preparation of Example 9.

Example 10

In the same manner as in Example 9 except that 2,6-di-tert-butyl-4-methylphenol and sodium thiosulfate were not used, acrylic polymer B (42.1 parts), compound A (8.0 parts), IPM (33.1 parts), PGML (7.5 parts), lauromacrogol (4.0 parts), and ALCH (0.4 parts) were used, the patch preparation of Example 10 was obtained.

Example 11

In the same manner as in Example 10 except that acrylic polymer B (34.9 parts), IPM (26.9 parts), PGML (14.9 parts), and lauromacrogol (10.0 parts) were used, the patch preparation of Example 11 was obtained.

Example 12

In the same manner as in Example 9 except that 2,6-di-tert-butyl-4-methylphenol and sodium thiosulfate were not used, acrylic polymer B (39.6 parts), compound A (5.0 parts), IPM (35.0 parts), PGML (10.0 parts), levulinic acid (5.0 parts), lauromacrogol (5.0 parts), and ALCH (0.4 parts) were used, the patch preparation of Example 12 was obtained.

Example 12a

In the same manner as in Example 12 except that lauromacrogol was not used, acrylic polymer B (45.0 parts), IPM (33.7 parts), and ALCH (0.1 parts) were used, and 2,6-di-tert-butyl-4-methylphenol (1.0 part) and sodium thiosulfate (as anhydrate) (0.13 parts) were added, the patch preparation of Example 12a was obtained.

Example 13

In the same manner as in Example 12 except that lauromacrogol was not used, acrylic polymer B (45.0 parts), compound A (5.5 parts), IPM (33.2 parts), PGML (10.0 parts), levulinic acid (5.0 parts), and ALCH (0.1 parts) were used, and 2,6-di-tert-butyl-4-methylphenol (1.0 part) and sodium thiosulfate (as anhydrate) (0.08 parts) were added, the patch preparation of Example 13 was obtained.

Example 13a

In the same manner as in Example 13 except that IPM (32.2 parts), levulinic acid (6.0 parts), and sodium thiosulfate (as anhydrate) (0.13 parts) were used, the patch preparation of Example 13a was obtained.

Example 13b

In the same manner as in Example 13a except that IPM (31.2 parts) and levulinic acid (7.0 parts) were used, the patch preparation of Example 13b was obtained.

Example 14

In the same manner as in Example 12 except that acrylic polymer B (49.9 parts), compound A (6.5 parts), IPM (23.5 parts), PGML (10.0 parts), levulinic acid (3.0 parts), lauromacrogol (7.0 parts), and ALCH (0.1 parts) were used, the patch preparation of Example 14 was obtained.

Example 15

In the same manner as in Example 12 except that PGML and lauromacrogol were not used, and acrylic polymer B (36.9 parts), compound A (8.0 parts), IPM (49.8 parts), levulinic acid (5.0 parts), and ALCH (0.4 parts) were used, the patch preparation of Example 15 was obtained.

Comparative Example 9

In the same manner as in Example 10 except that PGML, levulinic acid, and lauromacrogol were not used, and acrylic polymer B (49.9 parts), compound A (5.0 parts), IPM (45.0 parts), and ALCH (0.1 parts) were used, the patch preparation of Comparative Example 9 was obtained.

Comparative Example 10

In the same manner as in Comparative Example 9 except that acrylic polymer B (49.8 parts), compound A (8.0 parts), IPM (41.8 parts), and ALCH (0.4 parts)) were used, the patch preparation of Comparative Example 10 was obtained.

Comparative Example 11

In the same manner as in Example 12 except that lauromacrogol was not used, and acrylic polymer B (34.9 parts), compound A (2.0 parts), IPM (42.8 parts), PGML (14.9 parts), levulinic acid (5.0 parts), and ALCH (0.4 parts) were used, the patch preparation of Comparative Example 11 was obtained.

<Evaluation Test>

The preparations produced in the above-mentioned Examples and Comparative Examples were subjected to the evaluation of Experimental Example 3. The results are shown in Tables 6 and 7.

Example 16

To compound A (4.0 parts) were added PGML (10.0 parts), lauromacrogol (5.0 parts), and levulinic acid (5.0 parts) and the mixture was mixed and dissolved. Gelled hydrocarbon (HICALL gel (registered trade mark), KANEDA Co., Ltd.) (76.0 parts) was added, and the mixture was mixed and kneaded until it became homogeneous to give the ointment of Example 16.

Example 17

In the same manner as in Example 16 except that IPM (15.0 parts) was added, and compound A (5.0 parts) and gelled hydrocarbon (HICALL gel (registered trade mark), KANEDA Co., Ltd.) (60.0 parts) were used, the ointment of Example 17 was obtained.

Example 17a

In the same manner as in Example 16 except that oleic acid (20.0 parts) was added, and compound A (8.0 parts), levulinic acid (7.0 parts), and gelled hydrocarbon (HICALL gel (registered trade mark), KANEDA Co., Ltd.) (50.0 parts) were used, the ointment of Example 17a was obtained.

Example 18

In the same manner as in Example 16 except that oleic acid (25.0 parts) was added, and compound A (8.0 parts), levulinic acid (7.0 parts), and gelled hydrocarbon (HICALL gel (registered trade mark), KANEDA Co., Ltd.) (45.0 parts) were used, the ointment of Example 18 was obtained.

Example 19

In the same manner as in Example 16 except that oleic acid (20.0 parts) was added, and compound A (10.0 parts), levulinic acid (7.0 parts), and gelled hydrocarbon (HICALL gel (registered trade mark), KANEDA Co., Ltd.) (48.0 parts) were used, the ointment of Example 19 was obtained.

Comparative Example 12

To compound A (8.0 parts) was added oleic acid (42.0 parts) and the mixture was mixed and dissolved. Gelled hydrocarbon (HICALL gel (registered trade mark), KANEDA Co., Ltd.) (50.0 parts) was added, and the mixture was blended and kneaded until it became homogeneous to give the ointment of Comparative Example 12.

Comparative Example 13

In the same manner as in Example 16 except that PGML (10.0 parts) and lauromacrogol (5.0 parts) were added, and compound A (5.0 parts), oleic acid (25.0 parts), and gelled hydrocarbon (HICALL gel (registered trade mark), KANEDA Co., Ltd.) (55.0 parts) were used, the ointment of Comparative Example 13 was obtained.

<Evaluation Test>

The preparations produced in the above-mentioned Examples and Comparative Examples were subjected to the evaluation of Experimental Example 4 in which effective area was 10.25 mmφ and donor sample was 200 μL. The results are shown in Table 8.

TABLE 6

Effect of PGML, lauromacrogol on skin permeability

| | acrylic polymer B (parts) | compound A (parts) | IPM (parts) | PGML (parts) | levulinic acid (parts) | lauro-macrogol (parts) | 2,6-di-tert-butyl-4-methyl-phenol (parts) | sodium thio-sulfate (an-hydrous) (parts) | ALCH (parts) | skin permeability of compound A: cumulative permeation amount ($\mu g/cm^2/24$ h) | skin permeability of compound A: maximum permeation rate ($\mu g/cm^2/h$) | tack strength |
|---|---|---|---|---|---|---|---|---|---|---|---|---|
| Example 9 | 45.0 | 5.5 | 31.7 | 10.0 | 5.0 | 1.5 | 1.0 | 0.08 | 0.1 | 449.0 | 33.0 | — |
| Example 10 | 42.1 | 8.0 | 33.1 | 7.5 | 5.0 | 4.0 | — | — | 0.4 | 660.2 | 56.3 | good |
| Example 11 | 34.9 | 8.0 | 26.9 | 14.9 | 5.0 | 10.0 | — | — | 0.4 | 700.7 | 73.4 | good |
| Comparative Example 9 | 49.9 | 5.0 | 45.0 | — | — | — | — | — | 0.1 | 155.6 | 22.7 | — |

TABLE 6-continued

Effect of PGML, lauromacrogol on skin permeability

| | acrylic polymer B (parts) | compound A (parts) | IPM (parts) | PGML (parts) | levulinic acid (parts) | lauro-macrogol (parts) | 2,6-di-tert-butyl-4-methyl-phenol (parts) | sodium thio-sulfate (an-hydrous) (parts) | ALCH (parts) | skin permeability of compound A: cumulative permeation amount (μg/cm²/24 h) | skin permeability of compound A: maximum permeation rate (μg/cm²/h) | tack strength |
|---|---|---|---|---|---|---|---|---|---|---|---|---|
| Comparative Example 10 | 49.8 | 8.0 | 41.8 | — | — | — | — | — | 0.4 | 82.7 | 5.0 | — |

TABLE 7

Effect of compound A content on skin permeability

| | acrylic polymer B (parts) | compound A (parts) | IPM (parts) | PGML (parts) | levulinic acid (parts) | lauro-macrogol (parts) | 2,6-di-tert-butyl-4-methyl-phenol (parts) | sodium thio-sulfate (an-hydrous) (parts) | ALCH (parts) | skin permeability of compound A: cumulative permeation amount (μg/cm²/24 h) | skin permeability of compound A: maximum permeation rate (μg/cm²/h) | tack strength |
|---|---|---|---|---|---|---|---|---|---|---|---|---|
| Example 12 | 39.6 | 5.0 | 35.0 | 10.0 | 5.0 | 5.0 | — | — | 0.4 | 481.6 | 50.0 | — |
| Example 12a | 45.0 | 5.0 | 33.7 | 10.0 | 5.0 | — | 1.0 | 0.13 | 0.1 | 418.8 | 28.5 | — |
| Example 13 | 45.0 | 5.5 | 33.2 | 10.0 | 5.0 | — | 1.0 | 0.08 | 0.1 | 430.0 | 31.0 | — |
| Example 13a | 45.0 | 5.5 | 32.2 | 10.0 | 6.0 | — | 1.0 | 0.13 | 0.1 | 423.5 | 31.8 | — |
| Example 13b | 45.0 | 5.5 | 31.2 | 10.0 | 7.0 | — | 1.0 | 0.13 | 0.1 | 415.6 | 32.3 | — |
| Example 14 | 49.9 | 6.5 | 23.5 | 10.0 | 3.0 | 7.0 | — | — | 0.1 | 551.6 | 49.8 | — |
| Example 15 | 36.9 | 8.0 | 49.8 | — | 5.0 | — | — | — | 0.4 | 596.3 | 46.5 | good |
| Comparative Example 11 | 34.9 | 2.0 | 42.8 | 14.9 | 5.0 | — | — | — | 0.4 | 133.6 | 10.0 | bad |

TABLE 8

Skin permeability test of ointment (plate method)

| | gelled hydro-carbon (parts) | compound A (parts) | IPM (parts) | PGML (parts) | lauro-macrogol (parts) | levulinic acid (parts) | oleic acid (parts) | skin permeability of compound A: cumulative permeation amount (μg/cm²/24 h) | skin permeability of compound A: maximum permeation rate (μg/cm²/h) |
|---|---|---|---|---|---|---|---|---|---|
| Example 16 | 76.0 | 4.0 | — | 10.0 | 5.0 | 5.0 | — | 2283.2 | 95.1 |
| Example 17 | 60.0 | 5.0 | 15.0 | 10.0 | 5.0 | 5.0 | — | 3638.6 | 151.6 |
| Example 17a | 50.0 | 8.0 | — | 10.0 | 5.0 | 7.0 | 20.0 | 2942.5 | 122.6 |
| Example 18 | 45.0 | 8.0 | — | 10.0 | 5.0 | 7.0 | 25.0 | 3270.4 | 136.3 |
| Example 19 | 48.0 | 10.0 | — | 10.0 | 5.0 | 7.0 | 20.0 | 4391.4 | 183.0 |
| Comparative Example 12 | 50.0 | 8.0 | — | — | | — | 42.0 | 274.1 | 11.4 |
| Comparative Example 13 | 55.0 | 5.0 | — | 10.0 | 5.0 | — | 25.0 | 397.5 | 16.6 |

From the results in Table 6, the following points are clear.

(1) Compared with Comparative Examples 9 and 10 not containing additive A group, the cumulative permeation amount and the maximum permeation rate were improved, and the skin permeability of compound A was remarkably improved in Examples 9 to 11 containing additive A group.

(2) It was found that propylene glycol fatty acid ester in the additive A group shows good skin permeability of compound A at an addition amount of 7.5 to 14.9 wt %.

(3) It was found that lauromacrogol as a surfactant shows good skin permeability of compound A at an addition amount of 1.5 to 10.0 wt %.

(4) It was found that good tack strength was shown in Examples 10 and 11 containing additive A group.

From the results in Table 7, the following points are clear.

(1) Compared with Comparative Example 11 in which the content of compound A was 2.0 wt %, the cumulative permeation amount and the maximum permeation rate were improved, and the skin permeability of compound A was improved in Examples 12 to 15 in which the content of compound A was not less than 5.0 wt %.

(2) According to Example 14, it was found that the effect of improving the skin permeability of compound A was observed under the condition where the content of levulinic acid in the additive A group was not less than 3.0 wt %.

(3) In Comparative Example 11, a good tack strength was not obtained. On the other hand, it was found that a good tack strength was shown in Example 15 containing additive A group.

From the results in Table 8, the following points are clear.

(1) Compared with Comparative Example 12 not containing additive A group, the cumulative permeation amount and the maximum permeation rate were improved, and the skin permeability of compound A was remarkably improved in Examples 16 to 19 containing additive A group.

(2) Compared with Example 17a, the cumulative permeation amount and the maximum permeation rate were improved, and the skin permeability of compound A was improved in Example 18, and it was found that the skin permeability of compound A is improved by increasing the content of oleic acid used in combination with levulinic acid.

(3) In Comparative Example 13 not containing levulinic acid, the cumulative permeation amount and the maximum permeation rate were improved only slightly compared with Comparative Example 12.

Example 20

Using acrylic polymer B (39.6 parts), compound A (5.0 parts), IPM (35.0 parts), PGML (10.0 parts), levulinic acid (5.0 parts), lauromacrogol (5.0 parts), and ALCH (0.4 parts), a coating solution was obtained in the same manner as in Example 9. 2,6-di-tert-Butyl-4-methylphenol (0.05 parts) was dissolved in an appropriate amount of methanol, the coating solution obtained above was added to a total amount of 100 parts, and the patch preparation of Example 20 was obtained in the same manner as in Example 9.

Example 21

In the same manner as in Example 20 except that 2,6-di-tert-butyl-4-methylphenol was not used, and sodium thiosulfate (as anhydrate) (0.13 parts) was dissolved in an appropriate amount of water for injection and added, the patch preparation of Example 21 was obtained.

Example 22

In the same manner as in Example 20 except that 2,6-di-tert-butyl-4-methylphenol was not used, and 2-mercapto-benz imidazole (hereinafter to be referred to as "2-MBI") (0.62 parts) was dissolved in an appropriate amount of methanol and added, the patch preparation of Example 22 was obtained.

Example 23

In the same manner as in Example 20 except that 2,6-di-tert-butyl-4-methylphenol was not used, and propyl gallate (0.019 parts) was dissolved in an appropriate amount of methanol and added, the patch preparation of Example 23 was obtained.

Example 24

In the same manner as in Example 20 except that 2,6-di-tert-butyl-4-methylphenol was not used, and α-tocopherol (0.002 parts) was dissolved in an appropriate amount of methanol and added, the patch preparation of Example 24 was obtained.

Example 25

In the same manner as in Example 20 except that 2,6-di-tert-butyl-4-methylphenol was not used, and sodium sulfite (as anhydrate) (0.2 parts) was dissolved in an appropriate amount of water and added, the patch preparation of Example 25 was obtained.

Example 26

In the same manner as in Example 20 except that 2,6-di-tert-butyl-4-methylphenol was not used, and sodium bisulfite (0.3 parts) was dissolved in an appropriate amount of water and added, the patch preparation of Example 26 was obtained.

Example 27

Using acrylic polymer B (48.9 parts), compound A (6.5 parts), IPM (23.5 parts), PGML (10.0 parts), levulinic acid (3.0 parts), lauromacrogol (7.0 parts), and ALCH (0.1 parts), 2,6-di-tert-butyl-4-methylphenol (1.0 part) was dissolved in an appropriate amount of methanol and added, and the patch preparation of Example 27 was obtained in the same manner as in Example 9.

Example 28

In the same manner as in Example 27 except that 2,6-di-tert-butyl-4-methylphenol was not used, acrylic polymer B (49.7 parts) was used, and 2-MBI (0.2 parts) was dissolved in an appropriate amount of methanol and added, the patch preparation of Example 28 was obtained.

Example 29

In the same manner as in Example 27 except that acrylic polymer B (48.7 parts) was used, 2,6-di-tert-butyl-4-methylphenol (1.0 part) was dissolved in an appropriate amount of methanol and added, and sodium thiosulfate (as anhydrate) (0.2 parts) was dissolved in an appropriate amount of water and added, the patch preparation of Example 29 was obtained.

Example 30

In the same manner as in Example 27 except that acrylic polymer B (48.7 parts) was used, and 2,6-di-tert-butyl-4-methylphenol (1.0 part) and 2-MBI (0.2 parts) were dissolved in an appropriate amount of methanol and added, the patch preparation of Example 30 was obtained.

Example 31

In the same manner as in Example 9 except that acrylic polymer B (45.0 parts), compound A (5.5 parts), IPM (33.2 parts), PGML (10.0 parts), levulinic acid (5.0 parts), ALCH (0.1 parts), and 2,6-di-tert-butyl-4-methylphenol (1.0 part) were used, and sodium thiosulfate (anhydrate) (0.08 parts) was dissolved in an appropriate amount of water and added, the patch preparation of Example 31 was obtained.

Example 32

In the same manner as in Example 31 except that sodium thiosulfate (as anhydrate) (0.13 parts) was used, the patch preparation of Example 32 was obtained.

Example 33

In the same manner as in Example 31 except that IPM (31.7 parts) was used, and lauromacrogol (1.5 parts) was added, the patch preparation of Example 33 was obtained.

Example 34

In the same manner as in Example 32 except that IPM (31.7 parts) was used, and lauromacrogol (1.5 parts) was added, the patch preparation of Example 34 was obtained.

Comparative Example 14

In the same manner as in Example 9 except that acrylic polymer B (39.6 parts), compound A (5.0 parts), IPM (35.0 parts), PGML (10.0 parts), levulinic acid (5.0 parts), lauromacrogol (5.0 parts), and ALCH (0.4 parts) were used, the patch preparation of Comparative Example 14 was obtained.

Comparative Example 15

In the same manner as in Example 20 except that 2,6-di-tert-butyl-4-methylphenol was not used, and L-ascorbyl palmitate (0.013 parts) was dissolved in an appropriate amount of methanol and added, the patch preparation of Comparative Example 15 was obtained.

Comparative Example 16

In the same manner as in Example 20 except that 2,6-di-tert-butyl-4-methylphenol was not used, and L-ascorbic acid (0.1 parts) was dissolved in an appropriate amount of methanol and added, the patch preparation of Comparative Example 16 was obtained.

Comparative Example 17

In the same manner as in Example 27 except that 2,6-di-tert-butyl-4-methylphenol was not used, and acrylic polymer B (49.9 parts) was used, the patch preparation of Comparative Example 17 was obtained.

<Evaluation Test>

The preparations produced in the above-mentioned Examples and Comparative Examples were subjected to the following test. The results are shown in Tables 10 and 11.

Experimental Example 5: Stability Test of Preparation

Samples of the preparation containing various stabilizers were stored under stress conditions (at 60° C. for 2 weeks or at 50° C. for one month), and the stability of the preparation was evaluated by the changes in the content of compound A in the preparation due to storage and the color difference of the preparation. In addition, in order to evaluate the stability of the preparation against light, the preparation was stored under exposure conditions (total irradiance 53000 lx·h, irradiance 2000 lx, radiation time 26.5 h), and the content of the compound in the preparation was measured. The content of compound A was measured by the following method.

[Content of Compound A]

Under the following conditions, the peak area corresponding to the drug (Compound A) when analyzed by HPLC was calculated as an area percentage % from the HPLC chart.

Mobile phase A: diluted phosphate buffer (0.05 mol, pH 6.8)

Mobile phase B: acetonitrile for HPLC

Detector: ultraviolet absorption spectrophotometer (measurement wavelength: 245 nm)

Column: A stainless steel tube with an inner diameter of 4.6 mm and a length of 10 cm is filled with octadecylsilylated silica gel for HPLC (XBridge C18 or equivalent)

Mobile phase liquid feed: The mixing ratio of mobile phase A and mobile phase B is changed as shown in Table 9 to control the density gradient.

TABLE 9

| time (min) after injection | mobile phase A (vol %) | mobile phase B (vol %) |
|---|---|---|
| 0-19 | 90→30 | 10→70 |
| 19-28 | 30 | 70 |

Fed at the initial mixing ratio from 28 min to 35 min.

[Color Difference]

The preparation was placed on a standard white plate, and the b* value was measured using a color difference meter (CR-400, Konica Minolta, Inc.).

TABLE 10

Effect of antioxidant on preservation stability (preparation formulation: acrylic polymer B 39.4 to 39.6%/compound A 5%/IPM 35%/PGML 10%/levulinic acid 5%/lauromacrogol 5%/ALCH 0.4%)

| | | | | | | | | | | stress test | | |
|---|---|---|---|---|---|---|---|---|---|---|---|---|
| | 2,6-di-tert-butyl-4-methyl-phenol (parts) | sodium thio-sulfate (an-hydrate) (parts) | 2-MBI (parts) | propyl gallate (parts) | α-toco-pherol (parts) | sodium sulfite (an-hydrous) (parts) | sodium bi-sulfite (parts) | L-ascorbyl palmitate (parts) | L-ascorbic acid (parts) | preparation storage conditions | content (area percenttage) | color difference (b* value) |
| Example 20 | 0.05 | — | — | — | — | — | — | — | — | 60° C./ | 98.5 | 5.6 |
| Example 21 | — | 0.13 | — | — | — | — | — | — | — | 2 weeks | 99.3 | 7.7 |
| Example 22 | — | — | 0.62 | — | — | — | — | — | — | | 99.4 | 4.3 |
| Example 23 | | | | 0.019 | — | — | — | — | — | | 98.7 | 7.9 |

TABLE 10-continued

Effect of antioxidant on preservation stability (preparation formulation: acrylic polymer B 39.4 to 39.6%/compound A 5%/IPM 35%/PGML 10%/levulinic acid 5%/lauromacrogol 5%/ALCH 0.4%)

| | 2,6-di-tert-butyl-4-methylphenol (parts) | sodium thiosulfate (anhydrate) (parts) | 2-MBI (parts) | propyl gallate (parts) | α-tocopherol (parts) | sodium sulfite (anhydrous) (parts) | sodium bisulfite (parts) | L-ascorbyl palmitate (parts) | L-ascorbic acid (parts) | stress test preparation storage conditions | content (area percenttage) | color difference (b* value) |
|---|---|---|---|---|---|---|---|---|---|---|---|---|
| Example 24 | — | — | — | — | 0.002 | — | — | — | — | | 97.4 | 6.9 |
| Example 25 | — | — | — | — | — | 0.2 | — | — | — | | 97.7 | 8.5 |
| Example 26 | — | — | — | — | — | — | 0.3 | — | — | | 98.0 | 6.8 |
| Comparative Example 14 | — | — | — | — | — | — | — | — | — | | 95.9 | 9.6 |
| Comparative Example 15 | — | — | — | — | — | — | | 0.013 | — | | 96.9 | 10.5 |
| Comparative Example 16 | — | — | — | — | — | — | — | — | 0.1 | | 97.5 | 9.6 |

TABLE 11

Preservation stabilizing effect by combination of antioxidants

| | acrylic polymer B (parts) | compound A (parts) | IPM (parts) | PGML (parts) | levulinic acid (parts) | lauromacrogol (parts) | ALCH (parts) | 2,6-di-tert-butyl-4-methylphenol (parts) | sodium thiosulfate (anhydrate) (parts) | 2-MBI (parts) | stress test preparation storage conditions | stress test content of compound A (area percenttage) | exposure test preparation storage conditions | exposure test content of compound A (area percenttage) |
|---|---|---|---|---|---|---|---|---|---|---|---|---|---|---|
| Ex. 27 | 48.9 | 6.5 | 23.5 | 10.0 | 3.0 | 7.0 | 0.1 | 1.0 | — | — | 60° C./2 weeks | 98.9 | 53000 lx · h | 99.3 |
| Ex. 28 | 49.7 | 6.5 | 23.5 | 10.0 | 3.0 | 7.0 | 0.1 | — | — | 0.2 | | 99.1 | | 99.6 |
| Ex. 29 | 48.7 | 6.5 | 23.5 | 10.0 | 3.0 | 7.0 | 0.1 | 1.0 | 0.2 | — | | 99.9 | | 99.8 |
| Ex. 30 | 48.7 | 6.5 | 23.5 | 10.0 | 3.0 | 7.0 | 0.1 | 1.0 | — | 0.2 | | 99.6 | | 99.7 |
| Ex. 31 | 45.0 | 5.5 | 33.2 | 10.0 | 5.0 | — | 0.1 | 1.0 | 0.08 | — | 50° C./1 month | 100.0 | | 99.9 |
| Ex. 32 | 45.0 | 5.5 | 33.2 | 10.0 | 5.0 | — | 0.1 | 1.0 | 0.13 | — | | 100.0 | | 100.0 |
| Ex. 33 | 45.0 | 5.5 | 31.7 | 10.0 | 5.0 | 1.5 | 0.1 | 1.0 | 0.08 | — | | 100.0 | | 99.9 |
| Ex. 34 | 45.0 | 5.5 | 31.7 | 10.0 | 5.0 | 1.5 | 0.1 | 1.0 | 0.13 | — | | 100.0 | | 99.9 |
| Com. Ex. 17 | 49.9 | 6.5 | 23.5 | 10.0 | 3.0 | 7.0 | 0.1 | — | — | — | 60° C./2 weeks | 96.6 | | 98.7 |

From the results in Table 10, the following points are clear.

(1) In Comparative Example 15 containing L-ascorbyl palmitate as a stabilizer in the adhesive layer, it was found that the content of compound A decreased and the b* value, which is an index of color difference, also increased by storage under stress conditions as in Comparative Example 14 not containing a stabilizer in the adhesive layer.

(2) In Comparative Example 16 containing L-ascorbic acid as a stabilizer in the adhesive layer, it was found that the decrease in the content of compound A was slightly suppressed but the b* value increased compared with Comparative Example 14 not containing a stabilizer in the adhesive layer.

(3) In contrast, it was found that the decrease in the content of compound A was suppressed and the increase in the b* value was also suppressed even by storage under stress conditions, in Examples 20 to 26 containing 2,6-di-tert-butyl-4-methylphenol, sodium thiosulfate, 2-MBI, propyl gallate, α-tocopherol, sodium sulfite, or sodium bisulfite as a stabilizer in the adhesive layer.

From the results in Table 11, the following points are clear.

(1) In Comparative Example 17 not containing a stabilizer in the adhesive layer, it was found that the content of compound A decreased under the thermal stress conditions and exposure conditions of the preparation. In contrast, it was found that the decrease in the content of compound A was suppressed in Examples 27 to 34 containing a stabilizer in the adhesive layer.

(2) It was also found that the stability of the preparation is remarkably improved by the combination of 2,6-di-tert-butyl methylphenol as a stabilizer and sodium thiosulfate or 2-MBI.

(3) It was found that the stabilizing effect on compound A in the preparation was maintained even under exposure conditions, by adding 2,6-di-tert-butyl-4-methylphenol, sodium thiosulfate, and 2-MBI alone or in combination as stabilizers.

INDUSTRIAL APPLICABILITY

According to the present invention, a tandospirone-containing transdermal absorption preparation that is superior in the skin permeability by containing levulinic acid, and can maintain a blood concentration sufficient to exhibit efficacy of tandospirone when in use can be provided. Furthermore, a tandospirone-containing transdermal absorption preparation (patch preparation) that is superior in the preservation stability and shows good skin permeability of tandospirone as an active ingredient drug can be provided by adding a specific additive to the preparation.

This application is based on a patent application No. 2020-026337 filed in Japan (filing date: Feb. 19, 2020) and a patent application No. 2020-132798 filed in Japan (filing date: Aug. 5, 2020), the contents of which are incorporated in full herein.

The invention claimed is:

1. A transdermal absorption preparation, comprising:

a transdermal absorption layer that comprises (i) tandospirone or a pharmaceutically acceptable salt thereof, (ii) levulinic acid or a pharmaceutically acceptable salt thereof, (iii) propylene glycol monocaprylate, propylene glycol monolaurate, or a combination thereof, and isopropyl myristate.

2. The transdermal absorption preparation according to claim 1, wherein the preparation is a patch preparation.

3. The transdermal absorption preparation according to claim 2, further comprising:

a backing film, wherein the transdermal absorption layer is an adhesive layer present on at least one surface of the backing film.

4. The transdermal absorption preparation according to claim 1, wherein the transdermal absorption layer comprises the (i) tandospirone.

5. The transdermal absorption preparation according to claim 1, wherein the transdermal absorption layer comprises the (i) tandospirone or a pharmaceutically acceptable salt thereof at a content of from 0.1 to 30 wt % with respect to 100 wt % of the transdermal absorption layer.

6. The transdermal absorption preparation according to claim 1, wherein the transdermal absorption layer comprises the (ii) levulinic acid.

7. The transdermal absorption preparation according to claim 1, wherein the transdermal absorption layer comprises the (ii) levulinic acid or a pharmaceutically acceptable salt thereof at a content of from 0.1 to 20 wt % with respect to 100 wt % of the transdermal absorption layer.

8. The transdermal absorption preparation according to claim 1, wherein the transdermal absorption layer comprises the (ii) levulinic acid or a pharmaceutically acceptable salt thereof at a content of from 3 to 10 wt % with respect to 100 wt % of the transdermal absorption layer.

9. The transdermal absorption preparation according to claim 1, wherein the transdermal absorption layer comprises the (ii) levulinic acid or a pharmaceutically acceptable salt thereof at a content of from 6 to 7 wt % with respect to 100 wt % of the transdermal absorption layer.

10. The transdermal absorption preparation according to claim 1, wherein a content of the (iii) propylene glycol monocaprylate, propylene glycol monolaurate, or a combination thereof in 100 wt % of the transdermal absorption layer is from 1 to 20 wt %.

11. The transdermal absorption preparation according to claim 1, wherein the transdermal absorption layer further comprises (iv) at least one additive selected from the group consisting of 2,6-di-tert-butyl-4-methylphenol, sodium thiosulfate, 2-mercaptobenzimidazole, propyl gallate, α-tocopherol, sodium sulfite, and sodium bisulfite.

12. The transdermal absorption preparation according to claim 11, wherein the (iv) at least one additive comprises 2,6-di-tert-butyl-4-methylphenol.

13. The transdermal absorption preparation according to claim 11, wherein the (iv) at least one additive comprises 2,6-di-tert-butyl-4-methylphenol, and a content of 2,6-di-tert-butyl-4-methylphenol in 100 wt % of the transdermal absorption layer is from 0.001 to 10 wt %.

14. The transdermal absorption preparation according to claim 11, wherein the (iv) at least one additive comprises sodium thiosulfate, and a content of sodium thiosulfate in 100 wt % of the transdermal absorption layer is from 0.001 to 7 wt % based on anhydrate.

15. The transdermal absorption preparation according to claim 11, wherein the (iv) at least one additive comprises 2,6-di-tert-butyl-4-methylphenol and sodium thiosulfate.

16. The transdermal absorption preparation according to claim 11, wherein the (iv) at least one additive comprises 2-mercaptobenzimidazole, and a content of 2-mercaptobenzimidazole in 100 wt % of the transdermal absorption layer is from 0.001 to 5 wt %.

17. The transdermal absorption preparation according to claim 11, wherein the (iv) at least one additive comprises propyl gallate, and a content of propyl gallate in 100 wt % of the transdermal absorption layer is from 0.001 to 7 wt %.

18. The transdermal absorption preparation according to claim 11, wherein the transdermal absorption layer comprises the (i) tandospirone, the (ii) levulinic acid, and the (iii) propylene glycol monocaprylate, propylene glycol monolaurate, or a combination thereof, and a content of the (i) tandospirone is from 0.1 to 30 wt %, a content of the (ii) levulinic acid is from 3 to 10 wt %, and a content of the (iii) propylene glycol monocaprylate, propylene glycol monolaurate, or a combination thereof is from 1 to 20 wt %, with respect to 100 wt % of the transdermal absorption layer.

19. The transdermal absorption preparation according to claim 1, wherein the transdermal absorption layer further comprises oleic acid.

* * * * *